US005837486A

United States Patent [19]
Bodary et al.

[11] Patent Number: 5,837,486
[45] Date of Patent: Nov. 17, 1998

[54] METHOD FOR PREPARING SOLUBLE ANALOGUES OF INTEGRINS

[75] Inventors: Sarah C. Bodary; Cornelia M. Gorman; John W. McLean, all of San Francisco; Mary A. Napier, Hillsborough, all of Calif.

[73] Assignee: Genentech, Inc., South San Francisco, Calif.

[21] Appl. No.: 445,443

[22] Filed: May 19, 1995

Related U.S. Application Data

[62] Division of Ser. No. 380,227, Jan. 30, 1995, abandoned, which is a continuation of Ser. No. 218,878, Mar. 28, 1994, abandoned, which is a continuation of Ser. No. 821,337, Jan. 13, 1992, abandoned, which is a continuation of Ser. No. 444,490, Dec. 1, 1989, abandoned, which is a continuation-in-part of Ser. No. 290,224, Dec. 22, 1988, abandoned.

[51] Int. Cl.$^6$ ................................................... C12N 15/12
[52] U.S. Cl. ...................................... 435/69.1; 435/69.7
[58] Field of Search ........................ 536/23.5; 435/69.1, 435/69.7, 240.2, 252.3, 320.1, 325, 326

[56] References Cited

U.S. PATENT DOCUMENTS 4,761,371  8/1988  Bell et al. ............................... 435/69.1

FOREIGN PATENT DOCUMENTS

| 139416 | 5/1985 | European Pat. Off. . |
| 244221 | 11/1987 | European Pat. Off. . |
| 244267 | 11/1987 | European Pat. Off. . |
| 278776 | 8/1988 | European Pat. Off. . |
| WO 89/00200 | 1/1989 | WIPO . |
| WO 91/19511 | 12/1991 | WIPO . |

OTHER PUBLICATIONS

Argraves et al., "Amino Acid Sequence of the Human Fibronectin Receptor" *Journal of Cell Biology* 105:1183–1190 (Sep. 1987).

Argraves et al., "cDNA Sequences from the α subunit of the fibronectin receptor predict a transmembrane domain and a short cytoplasmic peptide" *Journal of Biological Chemistry* 261(28):12922–12924 (Oct. 5, 1986).

Arnaout et al., "Expression of a soluble and functional form of the human B2 integrin CD11b/CD18" *Journal of Cell Biology* 111(5):768 (1990).

Arnaout, A. M., et al., "Amino acid sequence of the alpha subunit of human leukocyte adhesion receptor mol complement receptor type 3" *Journal of Cell Biology* 106:2153–2158 (1988).

Bennett et al., "Expression of Human Platelet Glycoprotein IIb in Cult. Mamm. Cells." *61st Scientific Sessions 1234* (1988).

Berman et al., "Biosynthesis and Function of Membrane Bound and Secreted Forms of Recombinant CD11b/CD18 (Mac–1)" *J. Cell. Biochem.* 52:183–195 (1993).

Bodary et al., "Expression of recombinant platelet glycoprotein IIbIIIa results in a functional fibrinogen–binding complex" *Journal of Biological Chemistry* 264(32):18859–18862 (1989).

Boulianne, G. L. et al., "Production of functional chimaeric mouse/human antibody" *Nature* 312(5995):643–646 (Dec. 1984).

Bray et al., "Physical linkage of the genes for platelet membrane glycoproteins IIb and IIIa" *Proc. Natl. Acad. Sci. USA* 85:8683–8687 (Nov. 1988).

Bray et al., "Platelet Glycoprotein IIb" *J. Clin. Invest.* 80:1812–1817 (Dec. 1987).

Buck and Horwitz, "Cell Surface Receptors for extracellular matrix molecules" *Ann. Rev. Cell Biol.* 3:179–205 (1987).

Chothia, "Principles that Determine the Structure of Proteins" *Annual Review of Biochem.* 53:537–572 (1984).

Cierniewski et al., "Palmitylation of the glycoprotein IIb–IIIa complex in human blood platelets" *Journal of Biological Chemistry* 264(21):12158–12164 (1989).

Corbi et al., "cDNA cloning and complete primary structure of the α subunit of a leukocyte adhesion glycoprotein" *EMBO Journal* 6(13):4023–4028 (1987).

Corbi et al., "The human leukocyte adhesion glycoprotein mac–1 (complement receptor type 3, CD11b) α subunit" *Journal of Biological Chemistry* 263(25):12403–12411 (1988).

Cosgrove et al., "A genomic clone encoding the α chain of the OKM1, LFA–1, and platelet glycoprotein IIb–IIIa molecules" *Proc. Natl. Acad. Sci. USA* 83:752–756 (1986).

Devlin et al., "Alteration of amino–terminal codons of human granulocyte–colony–stimulating factor increases expression levels and allows efficient processing by methionine aminopeptidase in *Escherichia coli*" *Gene* 65:13–22 (1988).

Doyle et al., "Analysis of progressive deletions of the transmembrane and cytoplasmic domains of influenza hemagglutinin" *Journal of Cell Biology* 103:1193–1204 (1986).

Doyle et al., "Mutations in the cytoplasmic domain of the influenza virus hemagglutinin affect different stages of intracellular transport" *Journal of Cell Biology* 100:704–714 (1985).

Early et al., "Two mRNAs can be produced from a single immunoglobulin μ Gene by alternative RNA processing pathways" *Cell* 20:313–319 (1980).

Falkner and Zachau, "Expression of mouse immunoglobulin genes in monkey cells" *Nature* 298:286–288 (1982).

(List continued on next page.)

*Primary Examiner*—John Ulm
*Assistant Examiner*—Karen E. Brown
*Attorney, Agent, or Firm*—Wendy M. Lee; Deirdre L. Conley

[57] ABSTRACT

Methods are provided for the preparation in recombinant host cells of biologically active soluble variants of discretely encoded, heteromultimer polypeptide receptors. Such variants are synthesized by the secretion from recombinant transformants of transmembrane-modified heteromultimer receptors. Preferred receptors are extracellular matrix, cell surface, or plasma protein-binding receptors such as GPIIb-IIIa.

15 Claims, 14 Drawing Sheets

OTHER PUBLICATIONS

Fisher et al., "HIV infection is blocked in vitro by recombinant soluble CD4" *Nature* 331:76–86 (1988).

Fitzgerald et al., "Comparison of cDNA–derived protein sequences of the human fibronectin and vitronectin receptor α–subunits and platelet glycoprotein IIb" *Biochemistry* 26:8158–8165 (1987).

Fitzgerald et al., "Protein Sequence of Endothelial Glycoprotein IIIa Derived from a cDNA Clone" *Journal of Biological Chemistry* 262:3936–3939 (1987).

Garoff, Henry, "Using recombinant DNA techniques to study protein targeting in the eucaryotic cell" *Ann. Rev. Cell Biol.* 1:403–445 (1985).

Gascoigne et al., "Secretion of a chimeric T–cell receptor–immunoglobulin protein" *Proc. Natl. Acad. Sci. USA* 84:2936–2940 (1987).

Gething & Sambrook, "Cell–surface expression of influenza haemagglutinin from a cloned DNA copy of the RNA gene" *Nature* 293:620–625 (1981).

Gething and Sambrook, "Construction of influenza haemagglutinin genes that code for intracellular and secreted forms of the protein" *Nature* 300:598–603 (1982).

Gething et al., "Expression of wild–type and mutant forms of influenza hemagglutinin: the role of folding in intracellular transport" *Cell* 46:909–950 (1986).

Gething et al., "Mutational analysis of the structure and function of the influenza virus hemagglutinin" *Current Topics in Membranes and Transport*, Academic Press, Chapter 2, vol. 23:17–41 (1985).

Ginsberg et al., "Cytoadhesins, integrins, and platelets" *Thromb. Haemost.* 59(1):1–6 (1988).

Groux et al., "Suppressor effects and cyclic AMP accumulation by the CD29 molecule of CD4+ lymphocytes" *Nature* 339:152–154 (1989).

Heidenreich et al., "Organization of the gene for platelet glycoprotein IIb" *Biochemistry* 29:1232–1244 (1990).

Hibbs et al., "The Cytoplasmic Domain of LFA–1 B subunit: sites required for binding . . . " *Journal of Experimental Medicine* 174:1227–1238 (Nov. 1991).

Holzmann et al., "Identification of a Murine Peyer's Patch–specific lymphocyte homing receptor as an integrin molecule with an α chain homologous to human VLA–4α" *Cell* 56:37–46 (1989).

Hurtley and Helenius, "Protein oligomerization in the endoplasmic reticulum" *Ann. Rev. Cell Biol.* 5:277–307 (1989).

Hynes, RO, "Integrins: A Family of Cell Surface Receptors" *Cell* 48:549–554 (1987).

Johnson et al., "Properties of the Insulin Receptor Ectodomain" *Proc. Natl. Acad. Sci, USA* 85:7516–7520 (1988).

Karnik et al., "Structure–function studies on bacteriorhodopsin" *Journal of Biological Chemistry* 262(19):9255–9263 (1987).

Kishimoto et al., "Cloning of the β Subunit of the Leukocyte Adhesion Proteins: Homology to an Extracellular Matrix Receptor Defines a Novel Supergene Family" *Cell* 48:681–690 (1987).

Kishimoto et al., "Leukocyte Adhesion Molecules" *Springer–Verlag* (Springer et al., ed.) p. 15.

Kohler, G., "Immunoglobulin chain loss in hybridoma lines" *Proc. Natl. Acad. Sci. USA* 77(4):2197–2199 (1980).

Kozak, M., "At least six nucleotides preceding the AUG initiator codon enhance translation in mammalian cells" *J. Mol. Biol.* 196:947–950 (1987).

Krangel et al., "Characterization of B Lymphoblastoid Cell Line Mutant that Secretes HLA–A2" *J. Immunol.* 132(6):2984–2991 (1984).

Larson et al., "Cloning of the alpha subunit of human LFA–1" *J. Cell. Biochem.* S11D:272 (1987).

Larson et al., "Primary structure of the leukocyte function–associated molecule–1 α subunit: an integrin with an embedded domain defining a protein superfamily" *Journal of Cell Biology* 108:703–712 (1989).

Loeb and Drickamer, "The chicken receptor for endocytosis of glycoproteins contains a cluster of N–acetylglucosamine–binding sites" *Journal of Biological Chemistry* 262(7):3022–3029 (1987).

Loftus et al., "Molecular cloning and chemical synthesis of a region of platelet glycoprotein IIb involved in adhesive function" *Proc. Natl. Acad. Sci. USA* 84:7114–7118 (1987).

MacKrell et al., "The lethal myospheroid gene of Drosophila encodes a membrane protein homologous to vertebrate integrin B subunits" *Proc. Natl. Acad. Sci. USA* 85:2633–2637 (Apr. 1988).

Mariuzza and Winter, "Secretion of a homodimeric VαCk T–cell receptor–immunoglobulin chimeric protein" *Journal of Biological Chemistry* 264(13):7310–7316 (1989).

Munro, "Uses of chimaeric antibodies" *Nature* 312:597 (1984).

Neuberger et al., "Recombinant antibodies possessing novel effector functions" *Nature* 312(5995):604–608 (Dec. 1984).

O'Toole et al, "Efficient surface expression of platelet GPI–Ib–IIIa Requires both subunits" *Blood* 74(1):14–18 (1989).

Owen and Lamb, "The T cell antigen receptor" *Immune Recognition* (IRL Press) pp. 37–42 (1988).

Phillips et al., "The Platelet Membrane Glycoprotein IIb–IIIa Complex" *Blood* 71(4):831–843 (1988).

Phillips et al., "The Platelet Membrane Glycoprotein IIb/IIIa Complex" *Annals N.Y. Acad. Sci.* 509:177–187 (1987).

Poncz et al., "Structure of the Platelet Membrane Glycoprotein IIb" *Journal of Biological Chemistry* 262(18):8476–8482 (Jun. 25, 1987).

Rogers et al., "Gene segments encoding transmembrane carboxyl termini of immunoglobulin gamma chains" *Cell* 26:19–27 (1981).

Rogers et al., "Two mRNAs can be produced from a single immunoglobulin $\mu$ gene by alternative RNA processing pathways" *Cell* 20:303–312 (1980).

Rosa et al., "Cloning of Glycoprotein IIIa cDNA from human erythroleukemia cells and localization of the gene to chromosome 17" *Blood* 72(2):593–600 (Aug. 1988).

Rose and Bergmann, "Expression from Cloned cDNA of Cell–Surface Secreted Forms of the Glycoprotein of Vesicular Stomatitis Virus in Eucaryotic Cells" *Cell* 30:753–762 (1982).

Rose and Doms, "Regulation of protein export from the endoplasmic reticulum" *Ann. Rev. Cell Biol.* 4:257–288 (1988).

Rouslahti et al., "New perspectives in cell adhesion: RGD and Integrins" *Science* 238:491–497 (1987).

Rupp et al., "Identical VB T–cell receptor genes used in alloreactive cytotoxic and antigen plus I–A specific helper T cells" *Nature* 315:425–427 (1985).

Sharon et al., "Expression of a $V_hC_k$ Chimaeric Protein in Mouse Myeloma Cells" *Nature* 309:364–367 (1984).

Smith et al., "Blocking of HIV–1 Infectivity by a Soluble, Secreted Form of the CD4 Antigen" *Science* 238:1704–1707 (1987).

Suzuki and Naitoh, "Amino acid sequence of a novel integrin B4 subunit and primary expression of the mRNA in epithelial cells" *EMBO Journal* 9(3):757–763 (1990).

Suzuki et al., "Amino acid sequence of the vitronectin receptor α subunit and comparative expression of adhesion receptor mRNSs*" *Journal of Biological Chemistry* 262(29):14080–14085 (Oct. 15, 1987).

Sveda et al., "Influenza virus hemagglutinin containing an altered hydrophobic carboxy terminus accumulates intracellularly" *Journal of Virology* 49(1):223–228 (1984).

Tamkun et al., "Structure of Integrin, a Glycoprotein Involved in the Transmembrane Linkage between Fibronectin and Actin" *Cell* 46:271–282 (1986).

Thiagarajan et al., "A human erythroleukemia cell line synthesizes a functionally active glycoprotein IIb–IIIa complex capable of binding fibrinogen" *Biochimica et Biophysica Acta* 924:127–134 (1987).

Traunecker et al., "Soluble CD4 molecules neutralize human immunodeficiency virus" *Nature* 331:84–86 (1988).

Van Driel et al., "Self–association of the low density lipoprotein receptor mediated by the cytoplasmic domain" *Journal of Biological Chemistry* 262(33):16127–16134 (1987).

Wills et al., "Mutations of the Rous Sarcoma Virus env Gene that affect the transport and subcellular location of the glycoprotein products" *Journal of Cell Biology* 99:2011–2033 (1984).

Yuan et al., "Cloning and sequence analysis of a novel β 2–related integrin transcript from T lymphocytes: homology of integrin cysteine–rich repeats to domain III of laminin B chains" *Int–Immunol* (published erratum appears in Int Immunol 1991 Dec;3(12):1373–4) 2(11):1097–1108 (1990).

Zimrin et al., "Structure of Platelet of Glycoprotein IIIa" *J. Clin. Invest.* 81:1470–1475 (May 1988).

```
         scrFI
         nciI
         mspI
scrFI
bstNI    taqI  fokI
         mnlI                                                        haeIII
                                                                     sau96I
                                                                     scrFI
                                                                     nciI         sau96I
                                                                     mspI         nlaIV        ppuMI  haeIII pflMI              scrFI
                                            fnu4HI                   hpaII        avaII        nlaIV  eaeI                      bstNI
                                            bbvI       alwNI                                          ecoO109I                  nlaIV 1201 CACCCCTGGGCGACCTGGACCGGGATGGCTACAATGACATTGCAGTGCTGCCCTACGGGGTCCCAGTGGCCGGGCCAAGTGGCCGGCCCAAGGACCC
     GTGGGGACCCGCTGGACCTGGCCCTACCGATGTTACTGTAACGTCACGACGGGGATGCCCCAGGGTCACCGGCCGGTTCACGACCACAAGGACCC
362    P  L  G  D  L  D  R  D  G  Y  N  D  I  A  V  A  A  P  Y  G  G  P  S  G  R  G  Q  V  L  V  F  L  G sau96I
                                    avaII
                                    ppuMI
                                    ecoO109I
                                    scrFI
                                    pflMI scrFI                                nlaIV
                                    bstNI bstNI                                banI
           mnlI                                                                mnlI             taqI
     mnlI  ddeI        mnlI alwNI                    alwNI                     taqI            accI  claI
1301 TCAGAGTGAGGGGCTGAGGTCACGTCCCTCCCACAGGCTCTGCCTTTGGCTCTCCTTCGGACGGTGCGTAGACATC
     AGTCTCACTCCCCGACTCCAGTGCAGGGAGGGTCCGAGAGGTGTCCGAGACGGAAACCGAAGAGGAAGCTCCACGGCATCGTAG
395    Q  S  E  G  L  R  S  R  P  S  Q  V  L  D  S  P  F  F  P  T  G  S  A  F  G  F  S  L  R  G  A  V  D  I ddeI
                                                                        espI
                                                                        aluI
                                     bstXI                              sacI
                                     haeIII                             hgiAI              mnlI      aluI
                                     sau96I scrFI                       bsp1286            haeIII    alwNI
             sau3AI                                                     rsaI banII         stuI      pflMI
             mboI         aluI       nlaIV  bstNI                              hphI haeI
             dpnI         mboII                                                fnu4HI
                                                                               bbvI
1401 GATGACAACGGATACCCAGACCTGATCGTGGGAGCTTACGGGGCCAACCAGGTGGCTCAGCGAGCTCAGTGTACAGAGCTCTGTGAAGCCCTCTGTCCAGCTAC
     CTACTGTTGCCTATGGGTCTGGACTAGCACCCTCGAATGCCCCGGTTGGTCCACGACAATGTCTCGAGTCGCAGTCACACTTCCGAGACAGTCGATG
428    D  D  N  G  Y  P  D  L  I  V  G  A  Y  G  A  N  Q  V  A  V  Y  R  A  Q  P  V  V  K  A  S  V  Q  L  L hinfI  hinfI                     ddeI       aluI              fokI              nlaIV
                              aluI          mnlI
                              mboII
1501 TGGTGCAAGATTCACTCAGTGAATCCTGCTGTCTGTCTGAAGACTGCTACCTCAGAACCAAGACACCCGTGCTTCAACATCCAGATGTGTGTTGGAGCCAC
     ACCACGTTCTAAGTGACTTAGGACGACAGACAGACACTTCTGACGATGGAGTCTTGGTTCTGTGGGCACGAAGTTGTAGGTCTACACAACCTCGGTG
462    V  Q  D  S  L  N  P  A  V  K  S  C  V  L  P  Q  T  K  T  P  V  S  C  F  N  I  Q  M  C  V  G  A  T
```

Fig. 1(e)

```
                                                              naeI
                                                              haeIII
                                                              sau96I
                                     fnu4HI
                                     bbvI  sau96I             scrFI             fnu4HI
                                     pstI  avaII              bstNI mspI        bbvI bsp1286
                              mnlI   fnu4HI       mspI              hpaII       fnu4HI banII
               ddeI    aluI   bbvI aluI pvuII     hpaII
     bsp1286
1601 TGGGCACACAACATTCCTCAGAAGCTATCCCTAAATGCCAGCTGACGTCAGCTGACCTGGGCTCTTCGGGGCCGGAAGAGCCCCGGCCGGGTGCTGCTGGGCTCTCAA
     ACCCGTGTTGTAAGGAGTCTTCGATAGGGATTTACGGTCGACTGCAGTCGACTGGACCCGAGAAGCCCCGGCCTTCTCGGGGCCGGCCCACGACGACCCAGAGTT
495  G  H  N  I  P  Q  K  L  S  L  N  A  E  L  Q  L  D  R  Q  K  P  R  Q  G  R  R  V  L  L  G  S  Q sau3AI
                    mboI
                    dpnI
                    xhoII                                                                           scrFI
                                                                             haeI                   nciI
                                                                             haeIII                 mspI
                                          alwI                               nlaIII                 hpaII
             nlaIV                        scrFI                              styI
                     banI                 bstNI                              ncoI       taqI  mnlI
1701 CAGGCAGGCACCACCCTGAACCTGGGCGGCGAAAGCACAGCCCCATCTGCCACACCACCATGGCCTTCTTCCGAGATGAGCAGACTTCCGGACA
     GTCCGTCCGTGGTGGGACTTGGACCCGCCGCTTTCGTGTCGGGGTAGACGGTGTGGTAGACGGTGTGGTACCGGAAGAAGCTCTACTCCGTCTGAAGGCCCTGT
528  Q  A  G  T  T  L  N  L  D  L  G  G  K  H  S  P  I  C  H  T  T  M  A  F  L  R  D  E  A  D  F  R  D  K bsp1286                                                   sau96I
              banII                                                     nlaIV              nlaIII
         ddeI                                                           haeIII
         espI                                                fnu4HI
         hgiAI               mnlI                            bbvI
     aluI bsp1286 mnlI
1801 AGCTGAGCCCCATTGTGCTCAGCTGTCAATGTGTCCCTACCGCCACGGAGGCTGAATGCTGCTGTGCATGGAGACACCATGTGCAGGA
     TCGACTCGGGGTAACACGAGTCGACAGTTACACAGGGATGGCGGTGCCTCCGACTTACCGACGACACGTACCTCTGTGGTACACGTCCT
562  L  S  P  I  V  L  S  L  N  V  S  L  P  P  T  E  A  G  M  A  P  A  V  V  L  H  G  D  T  H  V  Q  E nlaIV bsp1286
              scrFI              aluI         banII
                                 aluI
              hinfI bstNI   mboII  bsp1286
1901 GCAGACACGAATCGTCCTGGGACTGTGGGAAGATGACGTATGTGCCCCAGCTTCAGCTGCCAGCTGTGCACTGAGTTGCCCCCGGTTGGGCA
     CGTCTGTGCTTAGCAGGACCCTGACACCCTTCTACTGCATACACGGGGTCGAAGTCGACGGTCGACACGTGACTCAACCGGGGCCAACCCGT
595  Q  T  R  I  V  L  D  C  G  E  D  D  V  C  V  P  Q  L  Q  L  T  A  S  V  T  G  S  P  L  L  V  G  A
```

```
                                                                              mnlI
                                                       mnlI                   haeIII    sau3AI
                                                       haeIII  fnu4HI         stuI      mboI      pstI
              nlaIII                                   haeI    bbvI           haeI      dpnI      fnu4HI
     bstUI    styI                                                            mnlI      alwI      bbvI
     hinPI    ncoI
     hhaI     haeIII
     thaI     sau96I
     bstUI
     hinPI
     hhaI     fnu4HI
     bssHII   bbvI
2801 GATGGCGCGCGGGCAGCGGCCATGGTCACGGTGTGCCAGCTGCTGGCCTTCCTGTGGCTGCCCAGCCTCTACCAGAGGCCTCTGGATCAGTTTGTGCTGCAGTCGCAC
     CTACCGCGCGCCCGTCGCCGGTACCAGTGCCACACGGTCGACGACCGGAAGGACACCGACGGGTCTCCGGAGATGGTCTCCGGAGACCTAGTCAAACACGACGTCAGCGTG
895   M  A  R  G  Q  R  A  M  V  T  V  L  A  F  L  W  L  P  S  L  Y  Q  R  P  L  D  Q  F  V  L  Q  S  H haeIII
                                                                                                         sau96I
                                                                                                         scrFI
                                                                                                         nciI  styI
                                                                                          fnu4HI
                                                                                          bbvI    mspI
                                                          bsp1286                         aluI    hpaII
                                                          nlaIV      ddeI        mnlI     pvuII          mnlI
             nlaIII          mnlI           ddeI   banI   espI       avaI   aluI
2901 GCATGGTTCAACGTGTCCTCCTCCCTATGCCCTGCCCGTCAGCCTGCCCCGTCAGCCTGCCCCGTCAGCCTGCCCCGAGGGGAAGCTCAGGTGTGGACACAGCTCTCCGGGCCTTGGAGG
     CGTACCAAGTTGCACAGGAGGGGGGATACGCCACGGGCAGTCGGACGGGGCAGTCGGACGGGGCAGTCGGACGGGGCTCCCCTTCGAGTCCACACCTGTGTCGACAGGGCCGGAACCTCC
928  A  W  F  N  V  S  S  L  P  Y  A  V  P  P  L  S  L  P  R  G  E  A  Q  V  W  T  Q  L  R  A  L  E  E hphI    mseI
      mnlI    aluI  hindIII
3001 AGAGGTGATGAAAGCTT
     TCTCCACTACTTTCGAA
962   R  O
```

Fig.2(a)

```
                                                                                                    sau96I
                                                                                                    haeIII sau96I
                                                                                         nlaIV bsp1286
                                                                                 banII apaI
                                                                          eco0109I
                                        hgiAI                             mnlI
                   hgiAI       tth111I  bsp1286
         nlaIII    taqI        mnlI
   xbaI  fnu4HI    bsp1286 mnlI
 1 TCTAGAGCCGCCATGAGAGACACGTCCTCGACACTGTGCTGGCACTGGGAGCACTGGCTGCTGGTGTTGGAGTAGGAGGCCCAACA
   AGATCTCGGCGGTACTCTCTGTGCAGGAGCTGTGACACGACCGTGACCCTGACCGACGACCATCCTCCCGGTTGT
-26   M  R  A  R  P  R  R  P  L  W  A  T  V  L  A  L  G  A  L  A  G  V  G  G  P  N  I
                                                                                             ↑
              aluI
                        hgiAI                                              hgiAI      hphI
              sacI      bsp1286                                            sau96I
      mnlI              banII                               sp1286        haeIII
      thaI     hgiAI              alwNI        banII nlaIII bstNI                     bsp1286
      rsaI  bstUI       banII              scrFI                  eco0109I            banII  mnlI
101 TCTGTACCACGGCGAGGTGAGCTCCTGCCAGCAGTGCCTGGCCTGTGAGCCCCATGTGTGCCTGTGCTCTGATGAGGCCCTGCCTCTGGGCTCACCTCG
    AGACATGGTGCCGCTCCACACTCGAGGACGTCGTCACGGACCGGACACTCGGGGTACACACGGAGACTACTCCGGGACGAGACCCGAGTGGAGC
  5   C  T  T  R  G  V  S  S  C  Q  Q  C  L  A  V  S  P  M  C  A  W  C  S  D  E  A  L  P  L  G  S  P  R mnlI
                                                                   avaI
                                                                   sau96I
                                                                   haeIII
                                                           rsaI              ddeI
              hinfI                                  mnlI  scaI  mnlI eco0109I
                       bsp1286 hinfI taqI
201 CTGTGACCTGAAGGAGAATCTGCTGAAGGATAAACTGTGCCCCAGAATCCATGCAGTTCCCAGTGAGGCCCGAGTACTAGAGGACAGGCCCCTCAGC
    GACACTGGACTTCCTCTTAGACGACTTCCTATTGACACGGGGTCTTAGGTAGCTCAAGGGTCACTCACTCTCATGATCTCCTGTCCGGGAGTCG
 38   C  D  L  K  E  N  L  L  K  D  N  C  A  P  E  S  I  E  F  P  V  S  E  A  R  V  L  E  D  R  P  L  S xmnI
                                                    mboII
                                         eaeI       taqI nlaIV haeIII
                                         mspI  mspI
                                         hpaII hpaII          asuII
                    alwI bstNI      mnlI        hinfI                 foxI
301 GACAAGGGCTCTGGAGACAGCTCCCAGGTCACTCAAGTCAGTCCCCAGAGGATTGCACTCCGGCTCCGGCCAGATGATTCGAAGAATTTCTCCATCCAAG
    CTGTTCCCGAGACCTCTGTCGAGGGTCCAGTGAGTTCAGTCAGGGGTCTCCTAACGTGAGGCCGAGGCCGGTCTACTAAGCTTCTTAAAGAGGTAGGTTC
 71   D  K  G  S  G  D  S  S  Q  V  T  Q  V  S  P  Q  R  I  A  L  R  L  R  P  D  D  S  K  N  F  S  I  Q  V bsp1286
banII                scrFI
```

Fig.2(b)

```
                                                                  rsaI
                                                                  nlaIV
                                                                  kpnI
                                      sau3AI                      banI
                                      mboI        alwNI           scrFI
                           sau96I     foki        pflMI
                           avaII      nlaIII      dpnI   sfaNI    bstNI
             bspMI                    foki        sfaNI  foki     aluI
      bspMI  fnu4HI  mnlI
  401 TGCGGCAGGTGGAGGATTACCCTGTGGACATCTACTACTTGATGGACCTGTCTTACTGAGATGAAGGATGATCTGTGGAGCATCCAGAACCTGGTACCAA
      ACGCCGTCCACCTCCTAATGGGACACCTGTAGATGATGAACTACTGGACAGAATGAGTGACTTCCTACTAGACACCTGTAGTTCTTGGACCATGGTT
  105 R    Q    V    E    D    Y    P    V    D    I    Y    Y    L    M    D    L    S    Y    S    M    K    D    D    L    W    S    I    Q    N    L    G    T    K haeIII
               haeI                                     bspMI
               eaeI         sfaNI     aluI              hphI
      balI                                                              nlaIII
  501 GCTGGCCACCCAGATGCGAAAGCTCACCAGTAACCTGCGGATTGGCTTCGGGGCCATTTGTGGACAAGCCTGTGTCACCATACATGTATATCTCCCACCA
      CGACCGGTGGGTCTACGCTTTCGAGTGGTCATTGGACGCCTAACCGAAGCCCCGGTAAACACCTGTTCGGACACAGTGGTATGTACATATAGAGGGTGGT
  138 L    A    T    Q    M    R    K    L    T    S    N    L    R    I    G    F    G    A    F    V    D    K    P    V    S    P    Y    M    Y    I    S    P    P sau96I                                                                              hphI
      haeIII                                                                              bstEII
      taqI                                                                                scrFI
      eco0109I                              mboII  bspMI      nlaIII                      bstNI
      mnlI mnlI
  601 GAGGCCCTCGAAAACCCCTGCTATGATGATGAAGACAACCACCTGCTTCGCCATGTTGGCTACAAACACGTGCTAACTGACCAGGTGACCCGCTTCA
      CTCCGGGAGCTTTTGGGGACGATACTACTACTTCTGTTGGTGGACGAAGCGGTACAAACCGATGTTTGTGCACGATTGACTGGTCCACTGGGCGAAGT
  171 E    A    L    E    N    P    C    Y    D    M    K    T    T    C    L    P    M    F    G    Y    K    H    V    L    T    L    T    D    Q    V    T    R    F    N mboII              nlaIV  sfaNI             sfaNI  nlaIII
      mnlI                               pflMI
  701 ATGAGGAAGTGAAGAAGCAGAGTGTCACGGAACCGAGATGCCCAGAGGGTGCCTTTGATGCCATCATGCAGGCTACAGTCTGTGATGAAAAGATTGG
      TACTCCTTCACTTCTTCGTCTCACAGTGCCTTGGCTCTACGGGTCTCCCACCGAAACTACGGTAGTACGTCCGATGTCAGACTACTTTTCTAACC
  205 E    E    V    K    K    Q    S    V    S    R    N    R    D    A    P    E    G    G    F    D    A    I    M    Q    A    T    V    C    D    E    K    I    G foki
                              sfaNI           pleI
                              nsiI            hinfI
                              avaIII  pflMI   sfaNI
      mnlI  sfaNI
  801 CTGGAGGAATGATGCATCCCACTTGCTGGCTTGTTACCACTGATGCCAAGACTCATATAGCATTGACGGAAGGCTGGCAGGCATTGTCCAGCCTAATGAC
      GACCTCCTTACTACGTAGGGTGAACGACCGAACAATGGTGACTACGGTTCTGAGTATATCGTAACTGCCTTCCGACCGTCCGTAACAGGTCGGATTACTG
  238 W    R    N    D    A    S    H    L    L    V    F    T    T    D    A    K    T    H    I    A    L    D    G    R    L    A    G    I    V    Q    P    N    D nlaIII
                                                             styI
                                              mnlI           ncoI
                                              bstXI
                      nlaIII                  mnlI                                   ddeI  aluI
  901 GGGCAGTGTCAGTTGGTAGTGACAATCATTACTCGCCTCCACTACCATGGATTATCCCTCTTTGGGCTGATGACTGAAGCTATCCCAGAAAAACA
      CCCGTCACAGTCAACCATCACTGTTAGTAATGAGACGGAGGTGATGGTACCTAATAGGGAGAAACCCGACTACTGACTTCGATAGGGTCTTTTTGT
  271 G    Q    C    H    V    G    S    D    N    H    Y    S    A    S    T    T    M    D    Y    P    S    L    G    L    M    T    E    K    L    S    Q    K    N    I
```

Fig.2(c)

```
                                                              sau96I
                                                              avaII
                                                        aluI
                                                        sacI foxI scrFI
                                                                  nlaIV                    nlaIII
                                                        hglAI bstNI                        styI
                                                        bsp1286                            ncoI hinfI
                                                        banII                                                       mboII
1001 TCAATTTGATCTTTGCAGTGACTGAAAATGTAGTCAATCTCTATCAGAACTATAGTGAGCTCATCCAGGAGGACCACAGTTGGGGTTCTCTGTCCATGGATTC
     AGTTAAACTAGAAACGTCACTGACTTTTACATCAGTTAGAGATATCACATCGAGTATCACTCGAGTAGGTCCCCTGGTGTCAACCCAAGACAGTACCTAAG
305  N   L   I   F   A   V   T   E   N   V   V   N   L   Y   Q   N   Y   S   E   L   I   P   G   T   T   V   G   V   L   S   M   D   S
                    sau3AI
                    mboI           mnlI aluI      sfaNI                                 mnlI
                    dpnI    alwNI                                        aluI
1101 CAGCAATGTCCTCCAGCTCATTGTGATGTTATGGGAAAATCCGTTCTAAAGTAGAGCTGGAAGTGCCTGACCTCCCTGAGAGAGTTGTCTATCCTTC
     GTCGTTACAGGAGGTCGAGTAACAATACGAATACCAATGCATTCATCTCGACCTTCACGCACTGGAGGACTTCTCAACAGATAGGAAG
338  S   N   V   L   Q   L   I   V   D   A   Y   G   K   I   R   S   K   V   E   L   E   V   R   D   L   P   E   E   L   S   L   F
                          haeIII                                                                               styI
                          scrFI
                       mnlI                                                              haeIII
                     bstNI                                                               haeI
                 bspMI      mnlI foxI haeI                               pleI            mnlI
1201 AATGCCACCTGCCTCAACAATGAGGTCATCCCTGGCCTCAAGTCTTGTATGGGACTCAAGATTGGAGACACGGTGAGCTTCAGCATTGAGGCCAAGGTGC
     TTACGGTGGACGGAGTTGTTACTCCAGTAGGGACCGGAGTTCAGAACATACCCTGAGTTCTAACCTCTGTGCCACTCGAAGTCGTAACTCCGGTTCCACG
371  N   A   T   C   L   N   N   E   V   I   P   G   L   K   S   C   M   G   L   K   I   G   D   T   V   S   F   S   I   E   A   K   V   R
                                                                                              hphI
         mnlI                                                                    scrFI
       scrFI                                                             sau3AI bstEII
      bstNI                                                                mboI
                                                                           dpnI bstNI                            bglI
1301 GAGGCTGTCCCCAGGAGAAGGAGAAGTCCTTCAAGGACGAGCCTGATCGTCCAGGTCACCTTTGATTGTGACTGTGCCTG
     CTCCGACAGGGGTCCTCTTCCTCTTCAGGAAGTTCCTGCTCGGACAGGTCCAGAGCTAGCAGTCCAGTGGAAACTAACACTGACACGGAC
405  G   C   P   Q   E   K   E   K   S   F   T   I   K   P   V   G   F   K   D   S   L   I   V   Q   V   T   F   D   C   D   C   A   C
                                                                                                              sau3AI
                                                                                                              mboI
                                                                                                              dpnI
                                                                                                              alwI
                                       sau96I                                                                 xhoII
                                       avaII                                                                  nlaIV
                                     ppuMI                                   scrFI
                                     nlaIV                                bstNI
          sau96I                     ecoO109I                             bglI                                bamHI
          haeIII                                                          haeIII                              alwI
    scrFI                                                                    sau96I
      bstNI    aluI           fnu4HI
1401 CCAGGCCCAAGCTGAACCTAATAGCCATCGCTGCAACAATGGCACCTTTGAGTGTGGGTATGCCGTTGTGGGCTGGCTGGCTGGATCCCAG
     GGTCCGGGTTCGACTTGGATTATCGGTAGCGACGTTGTTACCCGTTTACCCTGCGGAAACTAACTAACTACACCCATACGGCAACACCCGACCGACCCTAGGGTC
438  Q   A   Q   A   E   P   N   S   H   R   C   N   N   G   N   G   T   F   E   C   G   V   R   C   G   P   G   W   L   G   S   Q
```

```
            plel              msel                    sfaNI                      fokI        tth111I          rsaI
            hinfI     alul    aflII     bsrI   fokI            rsaI      mnlI           hinfI scaI
2001 CGAGATTGAGTCAGTGAAAGAGCTTAAGGACACTGGCAAGATGCAGTGAATTGTACCTATAAGAATGAGGATGACTGTCGTCAGATTCCAGTACTAT
     GCTCTAACTCAGTCACTTTCTCGAATTCCTGTGACCGTTCTACGTCACTTAACATGGATATTCTTACTCCTACTGACAGCAGTCTAAGGTCATGATA
 638  E   I   E   S   V   K   E   L   K   D   T   G   K   D   A   V   N   C   T   Y   K   N   E   D   D   C   V   V   R   F   Q   Y   Y
                                                                  sau96I
                                                                  haeIII
                                                                  sau96I
                                                                  nlaIV
                                                              ecoO109I
                                                              bsp1286                ddeI
                                                              banII                  sau3AI
                                                       apaI                          mboI
                                                       ecoO109I                      dpnI           alul
                                                              styI                   xhoII          msel
             hinfI          fokI             mboII                                          bglII hindIII
             mboII
2101 GAAGATTCTAGTGGAAAGTCCATCCTGTATGTGGTAGAAGAGCCAGAGTGTCCCAAGGGCCCTGACTGTGATGAGATCTAAGCTT
     CTTCTAAGATCACCTTTCAGGTAGGACATACACCATCTTCTCGGTCTCACAGGGTTCCCGGGACTGACACTACTCTAGATTCGAA
 671  E   D   S   S   G   K   S   I   L   Y   V   V   E   E   P   E   C   P   K   G   P   D   C   *
```

Fig. 3.

```
          XbaI
     EcoRI       10        20        30        40        50        60        70        80        90   ApaI  100
synthetic GAATTCTAGAGCGCCATGAGAGACCACGTCCTCGACCAGTCCTCTCTGGGCACTGCTGTCTGGAGCACTGGCTGGTGTTGGAGTAGGAGGGCCC
          *  *** ***  ** ** *****************  ** ** ***************** **  *****  ** *****  *********  *
natural   CGCCGCGGAGGCGGACGAGATGCGAGCGGGCCCGCCGCCCCCCGGCCGCCTCTGGGCGACTGTCTGGGCGCTGGCTGGCGTTGGCGTAGGAGGGC_C
               10        20        30        40        50        60        70        80        90   100
               M  R  A  R  P  R  P  L  W  A  T  V  L  A  L  G  A  L  A  G  V  G  G  P
```

METHOD FOR PREPARING SOLUBLE ANALOGUES OF INTEGRINS

CROSS REFERENCES

This application is a divisional of U.S. application Ser. No. 08/380,227 filed 30 Jan. 1995, abandoned, which application is a continuation of U.S. application Ser. No. 08/218,878 filed 28 Mar. 1994 (abandoned), which application is a continuation of U.S. application Ser. No. 07/821,337 filed 13 Jan. 1992 (abandoned), which application is a continuation of U.S. application Ser. No. 07/444,490 filed 1 Dec. 1989 (abandoned), which application is a continuation-in-part of U.S. application Ser. No. 07/290,224 filed 22 Dec. 1988 (abandoned), which applications are incorporated herein by reference and to which applications priority is claimed under 35 USC §120.

BACKGROUND OF THE INVENTION

This invention is concerned with the preparation of complex solubles receptors. In particular it is directed to the synthesis of recombinant receptors for cell matrix or plasma proteins.

Cellular membranes contain polypeptides which are lodged in the lipid bilayer. Such polypeptides contain a domain which anchors the protein in the cell membrane, a hydrophobic transmembrane domain, together in many instances with a C-terminal cytoplasmic sequence. In general, these polypeptides are single chain molecules or are multiple chain molecules derived from an ancestral single chain expression product by post-translational proteolytic processing. Such multiple chain polypeptides usually are covalently linked by disulfide bonds. However, some of these polypeptides are noncovalently associated with one another by salt bridges, Van der Waals forces, hydrophobic interactions and the like, and in such cases this association of polypeptide subunits into a larger aggregate is a prerequisite for biological activity.

The biological activity of such membrane-bound, multiple subunit molecules is varied, but in general reflects a receptor or binding function. Receptors serve to signal the cell regarding a condition or substance in the exterior environment of the cell, they serve to internalize an extracellular substance, or they function to attach cells to one another, to extracellular matrix substances, cell surface or plasma proteins.

A further subclass of membrane bound multiple subunit polypeptides are those in which each subunit is different, i.e. is not substantially homologous, and is encoded by a discrete gene. Such polypeptides are termed "MSP" (multiple subunit polypeptides) for the purposes of this invention. Numerous examples of such polypeptides or receptors are known, but the most substantial group is the class of cell surface receptors for extracellular matrix molecules, some of which have currently been identified and DNA encoding them cloned (see for example, Buck et al., "Ann. Rev. Cell Biol." 3:179 [1987] and Ruoslahti et al., "Science" 238: 491 [1987].)

Of particular interest is the platelet glycoprotein IIb-IIIa, a platelet membrane-bound receptor involved in platelet aggregation and which binds to fibrinogen, fibronectin, vitronectin and von Willebrand factor. The two subunits constituting this receptor have been cloned (Fitzgerald et al. "Biochemistry" 26:8158 [1987] and Fitzgerald et al. "J. Biol. Chem." 262(9):3936 [1987]). Bennett et al. reported expression of the GPIIb subunit in Cos-1 cells, but the subunit was not found on the cell membrane (AHA 61st Scientific Sessions, Nov. 15, 1988). Bennett et al. suggested that membrane localization might require the formation of the IIb-IIIa complex. There was no teaching or suggestion that a recombinant, membrane-bound GPIIb-IIIa, even if it could be made, would bind to its proper ligands, e.g., fibrinogen. In addition, an oral disclosure by Frelinger et al. at the same meeting purported to describe the transient expression of full length GPIIb-IIIa on an unidentified recombinant cell surface; no other information was provided relating to the manner in which expression was allegedly obtained.

Corbi et al. orally reported the transient expression of functional full length LFA-1 in COS cells in September 1988 at the Titisee Symposium sponsored by Boehringer Ingelheim.

Membrane-bound MSPs present difficulties in purification and stability since the hydrophobic domains tend to induce the MSPs to micelles or aggregates. A form of these receptors is needed that is soluble, particularly in body fluids such as blood and in pharmacological excipients such as saline, without forming multiple molecular aggregates beyond proper heterodimer assembly. Accordingly, it is an object herein to synthesize such MSP forms.

It is another object to produce soluble forms of the GPIIb-IIIa receptor which are capable of properly binding their normal ligands.

It is a further object to express GPIIIa in recombinant cell culture.

It is an additional object to produce high yields of GPIIb-IIIa from recombinant cell culture.

These and other objects will be apparent from consideration of this application as a whole.

SUMMARY

In accordance with this invention, a method is provided for the preparation of a secreted analogue of a cell membrane-bound multiple subunit polypeptide (MSP), each subunit of which is encoded by a discrete gene, comprising 1) introducing into the nucleic acid encoding each of the subunits a mutation encoding an amino acid sequence variant of the MSP that renders the MSP no longer capable of becoming lodged in a lipid bilayer, and 2) transfecting a host cell with the nucleic acid of step 1, 3) culturing the host cell of step 2 and 4) recovering from the host cell culture biologically active soluble MSP. Also in accordance with this invention, nucleic acid and expression vectors are provided which encode an amino acid sequence variant of an integrin chain, in particular a variant in which the transmembrane domain of the integrin chain is modified so that it is no longer capable of becoming lodged in the cell membrane.

Also provided is a method for the preparation of GPIIb-IIIa comprising transforming a permissive host cell with nucleic acid encoding GPIIb-IIIa and culturing the host cell until GPIIb-IIIa accumulates in the cell membrane.

In specific embodiments, the objects of this invention are accomplished by providing a biologically active MSP amino acid sequence variant selected from the group consisting of (a) an MSP amino acid sequence variant having an inactivated membrane anchor domain and (b) a polypeptide comprising an MSP extracellular domain fused to the sequence of a polypeptide which is different from the MSP, this latter, for example, selected from an immunogen or a protein with a long plasma half life such as an immunoglobulin constant domain.

In another embodiment, MSP amino acid residues or carbohydrate substituents of MSPs or MSP analogues otherwise described herein are derivatized by covalent modification or are conjugated to nonproteinaceous polymers such as polyethylene glycol to produce an MSP derivative which exhibits improved circulatory half life.

In particular embodiments a polypeptide comprising a biologically active extracellular domain of an integrin is fused at its C-terminus to an immunoglobulin constant domain, or is linked to an immunogenic polypeptide.

The MSP variants provided herein are purified and formulated in pharmacologically acceptable vehicles for diagnostic or preparatory utility or in vivo use in the modulation of cell adhesion.

BRIEF DESCRIPTION OF THE DRAWINGS

Figure 1A:
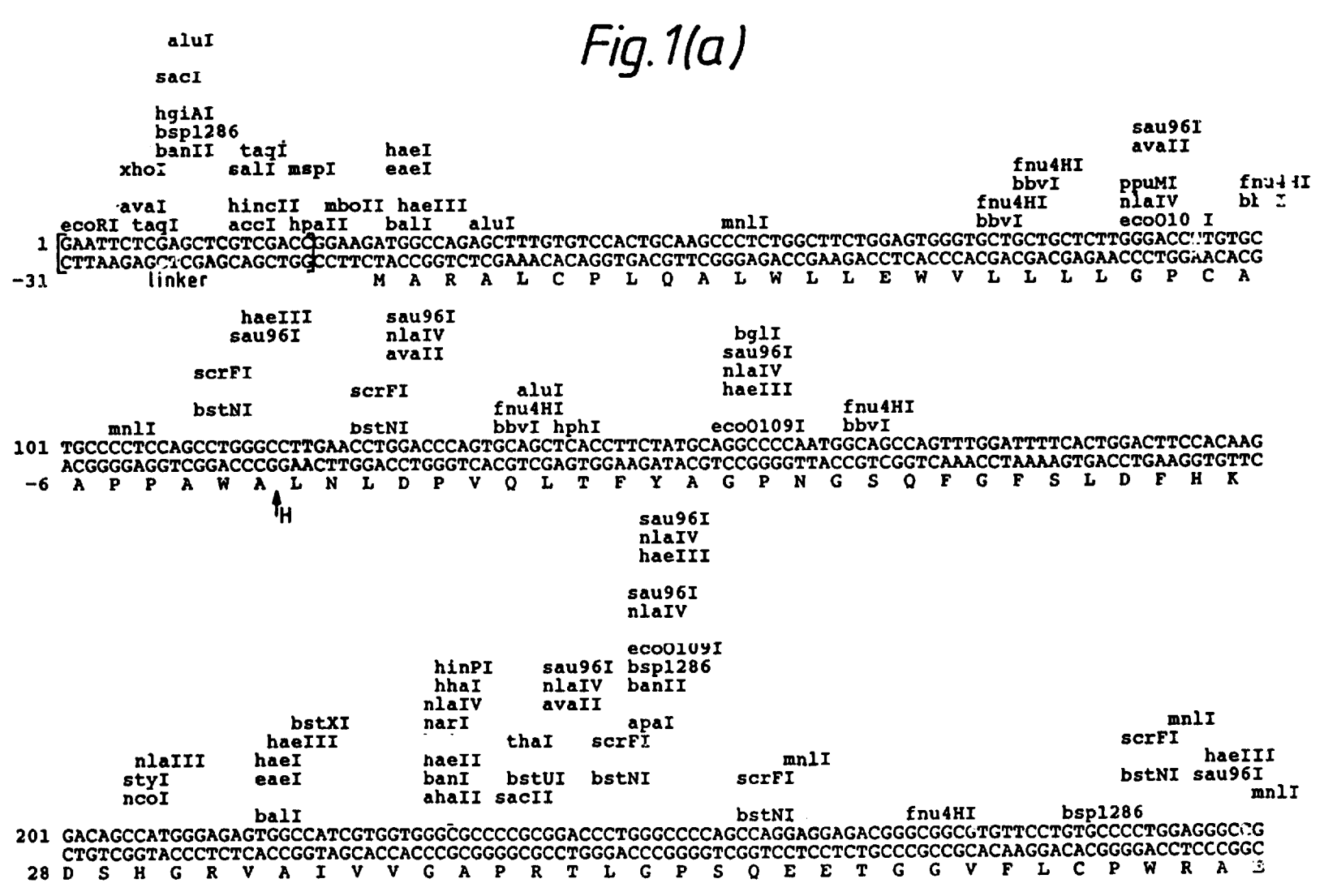
Figure 1B:
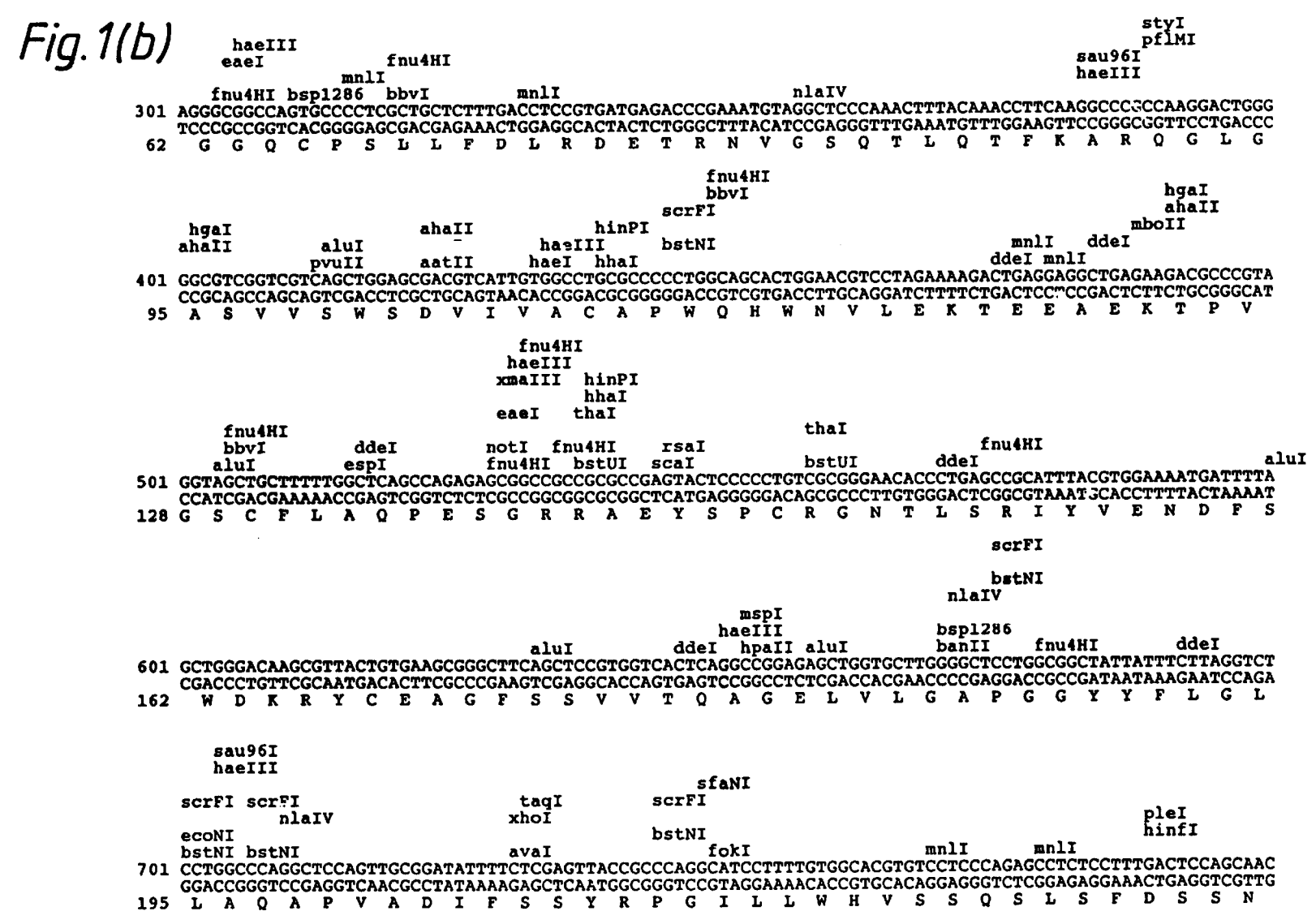
Figure 1C:
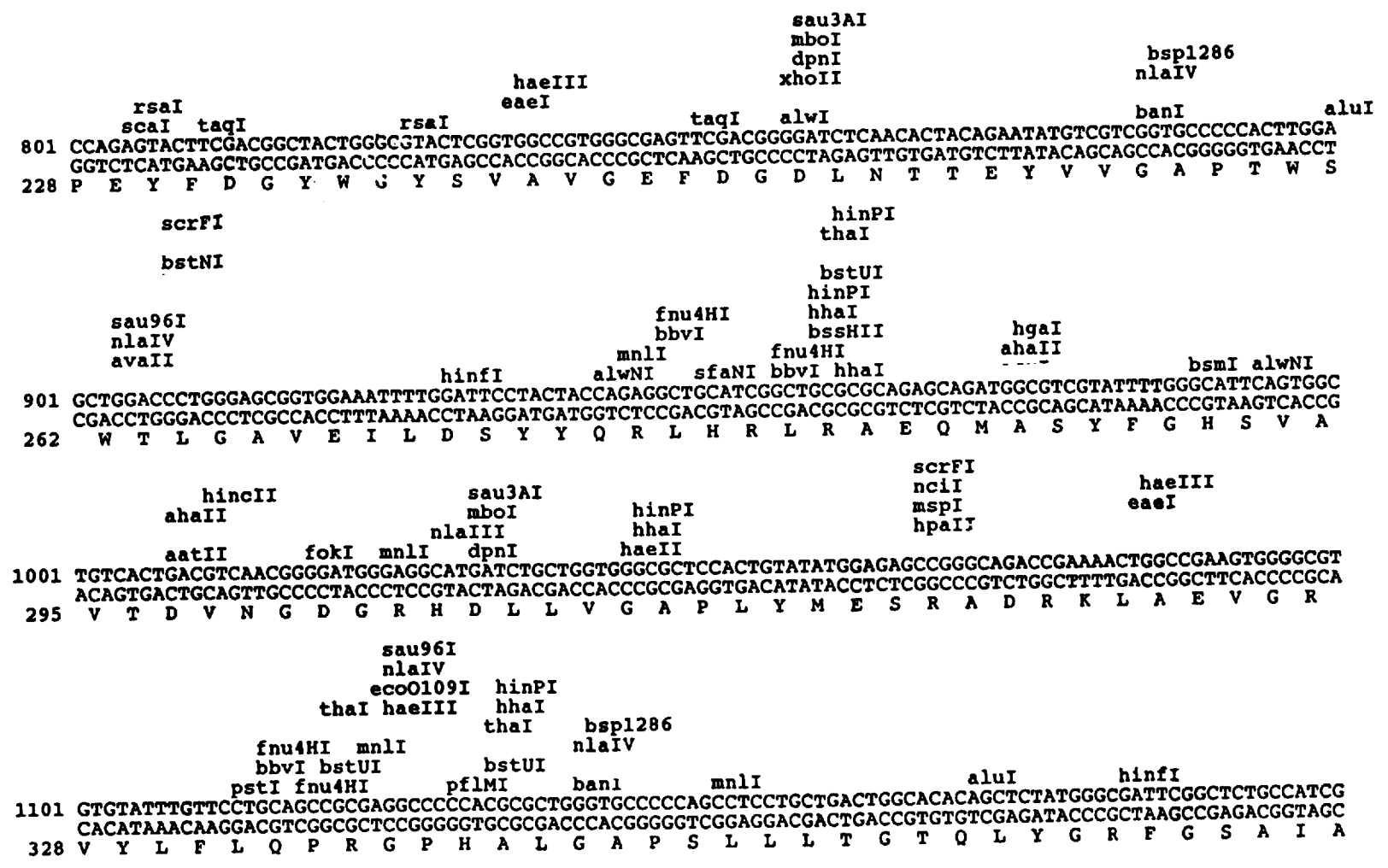
Figure 1F:
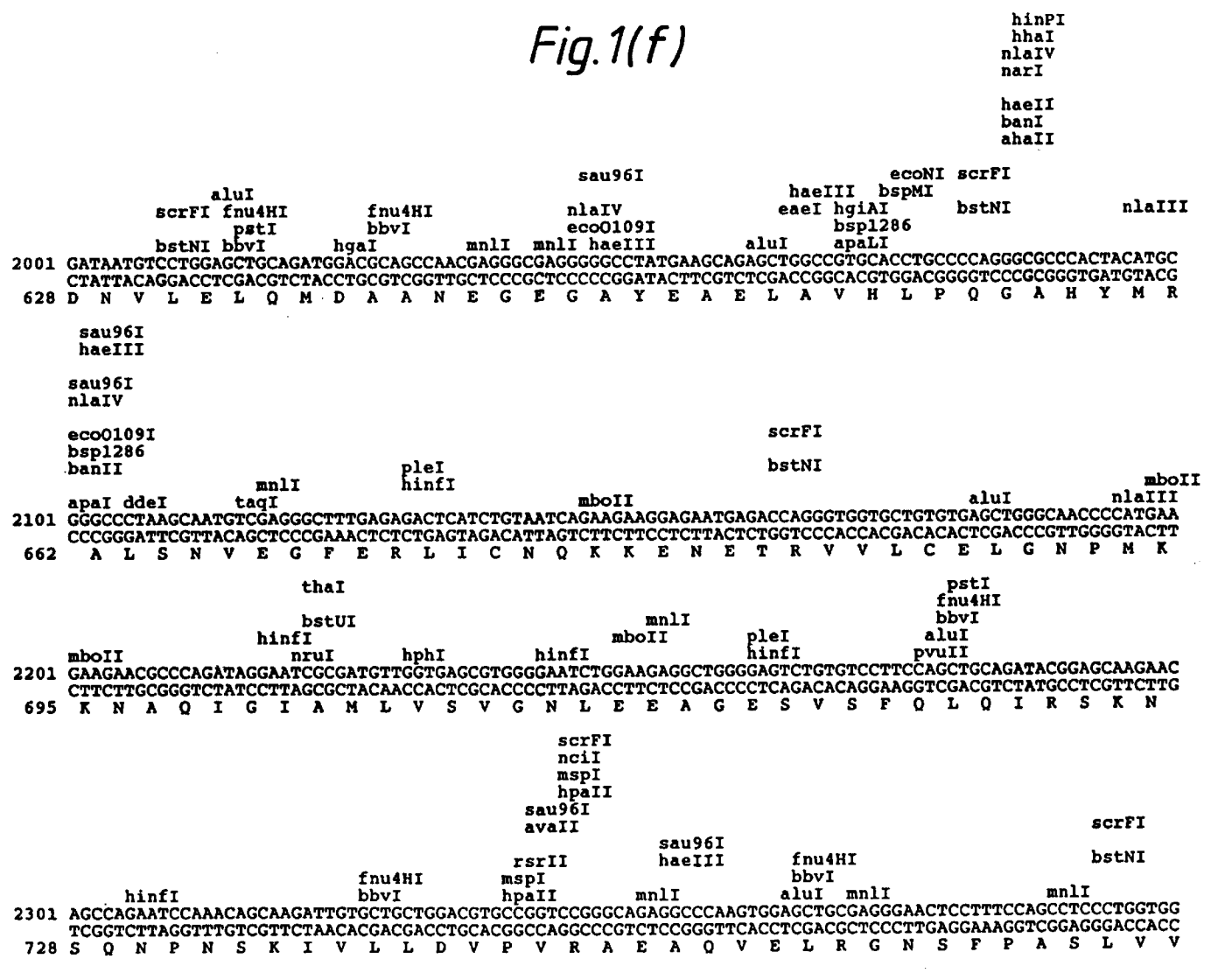
Figure 1G:
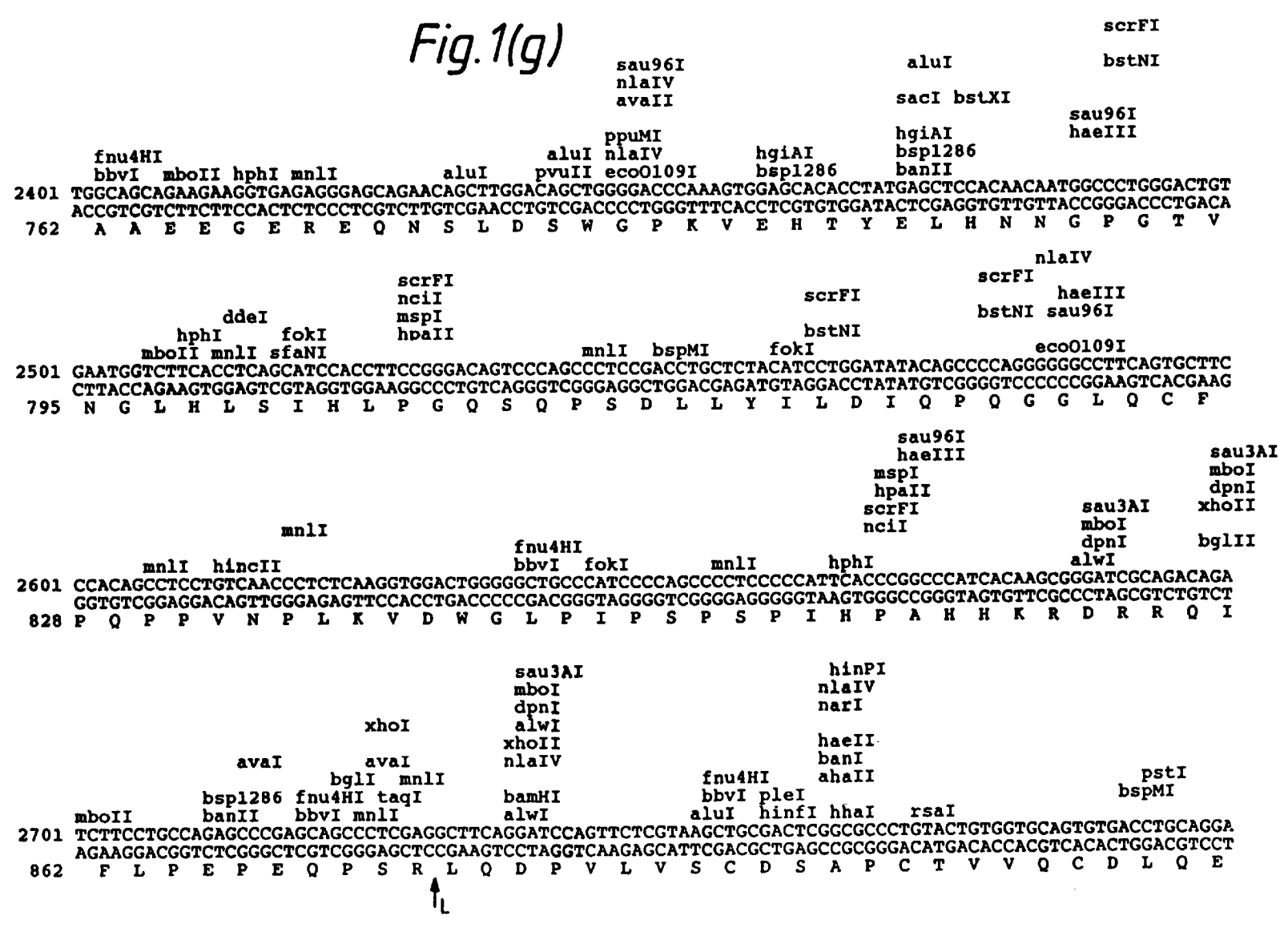

FIGS. 1(a)–1(h) depict the amino acid and nucleotide sequence of a secreted form of the GPIIb subunit of the MSP GPIIb-IIIa. The signal processing site for the heavy and light forms of this subunit are designated, respectively, with arrow-H and arrow-L.

Figure 2D:
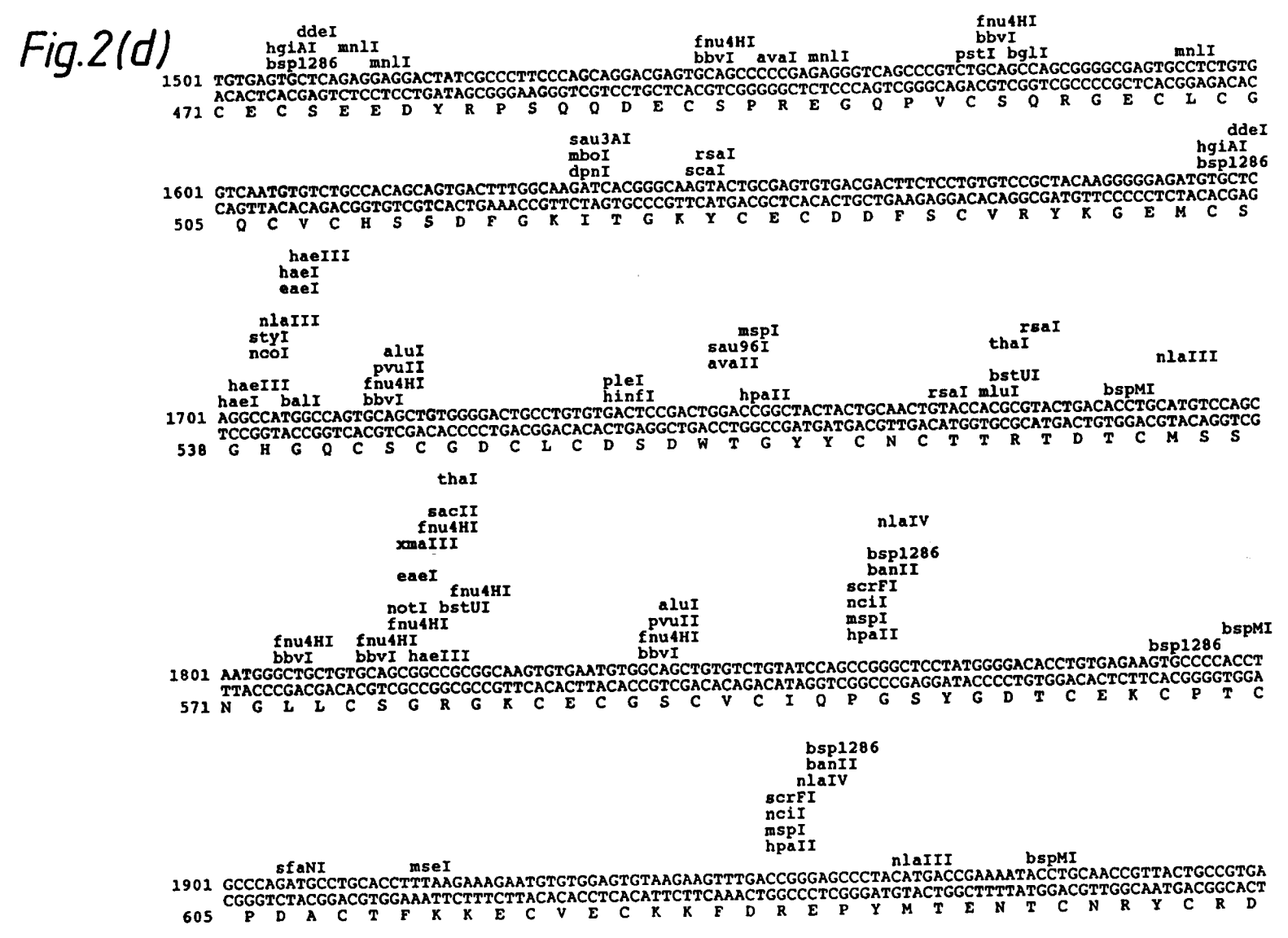

FIGS. 2(a)–2(e) depict the amino acid and nucleotide sequence of a secreted form of the GPIIIa subunit of the MSP GPIIb-IIIa. The signal processing site is designated with an arrow.

FIG. 3 depicts a comparison of the native and redesigned nucleic acid sequences at the 5' end of the GPIIIa gene.

DETAILED DESCRIPTION

An MSP is defined herein to be a multichain polypeptide, at least one chain of which is ordinarily anchored in a cell membrane and at least two chains of which are discretely encoded. MSPs ordinarily contain at least two distinct chains, two of which are lodged directly in the cell membrane. One or more additional chains may be covalently or noncovalently bound to the MSP chains ordinarily lodged in the cell membrane, but the additional chains may not themselves be anchored in the membrane. Such chains typically result from the post-translational processing of a single chain that becomes membrane anchored. Discretely encoded subunits are those which do not result from the posttranslational processing of a single translated protein, and their amino acid sequences are not homologous (i.e. the sequences of the subunits are not the same, and they do not assemble in nature into dimers or multimers of the same polypeptide). Instead, they are produced by the translation of independent mRNAs or polycistronic messages. Thus, the nucleic acids encoding MSP polypeptides ordinarily are found in nature under the control of different promoters and other transcription control sequences.

MSPs include principally cell surface receptors for extracellular matrix molecules, also defined as cellular adhesion receptors. Many of these receptors and their ligands, such ligands including the extracellular matrix molecules and plasma proteins such as fibrinogen as well as cell surface proteins such as I-CAM, are central to cellular adhesion phenomena involved in wound healing, morphogenic mobility, developmentally unrelated cellular migrations, hemostasis and metastasis. These cellular adhesion receptors are identified by functional and structural features. Functionally, they typically bind to polypeptides incorporating the sequence RGD, from which they are dissociated by competition with other polypeptides containing the RGD sequence such as the peptides RGDS or RGDV. Also, they frequently require a divalent cation such as calcium for ligand binding. MSPs may or may not include members of the immunoglobulin superfamily such as the T cell receptor. A group of MSPs involved in cell surface intracellular adhesive interactions have been designated integrins (see Buck et al., "Ann. Rev. Cell Biol." 3:179–205 [1987]).

Structurally, such cellular adhesion receptors belong to a supergene family of multimers in which a first single-chain polypeptide or disulfide cross-linked multi-chain polypeptide ($\alpha$-chain) is noncovalently associated with a second and different polypeptide (designated a $\beta$-chain), thereby forming a heteromultimer. The $\alpha$-chains of these receptors are quite diverse in terms of their amino acid sequence, and include the a subunit of avian integrin (band 1); $\alpha_1$, $\alpha_2$, and $\alpha_4$ of VLA 1, 2 and 4; $\alpha_3$ of VLA 3 and avian integrin (band 2); $\alpha_F$ of VLA 5 and the fibronectin receptor; $\alpha_L$ of LFA-1; $\alpha_M$ of Mac-1; $\alpha_X$ of p150,95; $\alpha_H \alpha_L$ of GPIIb; and $\alpha_V$ of vitronectin. The $\beta$-chains typically fall into three classes, $\beta_1$ (avian integrin [band 3]; fibronectin receptor and VLA), $\beta_2$ (LFA-1/Mac-1; p150,95) and $\beta_3$ (GPIIb-IIIa and vitronectin receptor), the members of each $\beta$-class being substantially homologous or identical. It is preferred that the MSP selected contain the two (or more) chains which ordinarily associate with one another in nature since non-naturally occurring heteromers may not form complexes.

Each chain of an MSP is expressed in its native environment as a preprotein comprising a secretion signal which is processed during the extracellular orientation of the receptor. Also, at least one chain of each subunit will have a hydrophobic anchor containing a polypeptide sequence serving as a site for covalent addition of lipid, e.g. phospholipid, or a domain located in the C-terminal portion of the polypeptide and containing about from 10 to 30 predominantly hydrophobic residues such as phe, leu, ile, val, met, gly and ala. Such membrane anchoring sequences or domains will be collectively referred to herein as membrane anchor domains. A short hydrophilic cytoplasmic domain, on the order of 10 to 100 residues, usually is found C-terminal to transmembrane domains. The term subunit should be understood to mean polypeptide chain; it does not refer to domains or functional subregions of a given polypeptide chain.

Certain MSPs share other structural features, for example, wherein one subunit of the receptor contains cysteine-rich tandem amino acid sequence repeats in which greater than about 80% of the cysteine residues are alignable within about two residues of the cysteine residues of the tandem repeats of GPIIIa, wherein one subunit has the consensus N-terminal sequence Tyr/Phe/Leu-Asn-Leu-Asp, or one subunit contains an amino acid domain having substantial sequence homology to the calmodulin calcium binding site.

Also included within the scope of MSPs are those receptors which are homologous to the above-described members of the integrin superfamily. Homologous, as defined herein, means having the sequence of a polypeptide of a member of the integrin superfamily which at least has substantially the same amino acid sequence homology to a known member of the superfamily as any presently known member has to any other known member. Typically, homologous means having greater than about 40% amino acid homology after aligning sequences for maximum homology, but not taking into account conservative substitutions.

This invention in part is based upon the discovery that discretely encoded MSPs, when modified to eliminate their ability to insert into the host cell membrane, nonetheless are fully assembled and secreted in biologically active form by recombinant host cells. Recombinant host cells secrete the subunits in correct association with one another such that the assembly exhibits the biological activity of the extracellular domain of the native MSP, despite the fact that proper association of the subunits is no longer facilitated by juxtaposition in the cell membrane. Further, proper assembly has been obtained even when the MSP sequences have not been fused to multimer-forming polypeptides, i.e. it has been found that MSPs will properly associate even without the aid of extraneous cross-linking polypeptides such as immunoglobulin chains.

Biological activity is defined in terms of the ability of the secreted MSP to qualitatively bind the ligand ordinarily bound by the MSP in its native environment, although it will be appreciated that the kinetics or other quantitative characteristics of ligand binding by the secreted MSP may vary from those of the native cell bound MSP. While secreted MSP most likely will retain many functional immune epitopes capable of cross-reacting with antibody raised against the native MSP, this alone is not enough for the secreted MSP to exhibit biological activity as defined herein; "biologically active" secreted MSP must exhibit the ability to bind to its ligand as well. However, it will be understood that not all MSP produced in accord with this invention need to exhibit biological activity in the sense defined here. Such biologically inactive but, for example, immunologically active MSP analogues find use in diagnostic assays, in raising antibodies against MSP, or in the purification of antibodies to MSP.

This invention is particularly concerned with amino acid sequence variants of MSPs. Amino acid sequence variants of MSPs are prepared with various objectives in mind, including increasing the affinity of the MSP for its binding partner, facilitating the stability, purification and preparation of the MSP (including enhanced water solubility and reduced membrane affinity), increasing its plasma half life, improving therapeutic efficacy as described above, introducing additional functionalities and lessening the severity or occurrence of side effects during therapeutic use of the MSP. Amino acid sequence variants of MSPs fall into one or a combination of the following classes: insertional, substitutional or deletional variants. Each MSP variant or analogue will have one inactivated membrane anchor domain, and this will be accomplished by insertion, substitution or deletion, but these variants optionally comprise additional mutations that are involved in other than inactivating the membrane anchor domain of one chain of the native MSP.

Insertional amino acid sequence variants are those in which one or more amino acid residues extraneous to the MSP are introduced into a predetermined site in the MSP including the C or N termini. Such variants are referred to as fusions of the MSP and a polypeptide containing a sequence which is other than that which is normally found in the MSP at the inserted position. Several groups of fusions are contemplated herein.

Immunologically active MSP fusions comprise an MSP and a polypeptide containing a non-MSP epitope. The non-MSP epitope is any immunologically competent polypeptide, i.e., any polypeptide which is capable of eliciting an immune response in the animal to which the fusion is to be administered or which is capable of being bound by an antibody raised against the non-MSP polypeptide. Typical non-MSP epitopes will be those which are borne by allergens, autoimmune epitopes, or other potent immunogens or antigens recognized by pre-existing antibodies in the fusion recipient, including bacterial polypeptides such as trpLE, beta-galactosidase, viral polypeptides such as herpes gD protein, and the like. Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the MSP or fragment thereof by a peptide bond(s). These products therefore consist of a linear polypeptide chain containing MSP epitopes and at least one epitope foreign to the MSP. It will be understood that it is within the scope of this invention to introduce the epitopes anywhere within the MSP molecule or fragment thereof. Such fusions are conveniently made in recombinant host cell or by the use of bifunctional cross-linking agents. The use of a cross-linking agent to fuse the MSP to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the MSP, which antibodies in turn are useful in diagnostics or in purification of MSP by immunoaffinity techniques known per se. Alternatively, in the purification of MSPs, binding partners for the fused non-MSP polypeptide, e.g. antibodies, receptors or ligands, are used to adsorb the fusion from impure admixtures, after which the fusion is eluted and, if desired, the MSP is recovered from the fusion, e.g. by enzymatic cleavage.

Other fusions, which may or may not also be immunologically active, include fusions of the mature MSP sequence with a signal sequence heterologous to the MSP, fusions of transmembrane-modified MSPs (including sequence deletions or modifications so that the MSP could not lodge in the cell membrane), for example, to polypeptides having enhanced plasma half life (ordinarily >about 20 hours) such as immunoglobulin chains or fragments thereof which confer enhanced plasma half life.

Signal sequence fusions are employed in order to more expeditiously direct the secretion of the MSP. The heterologous signal replaces the native MSP signal, and when the resulting fusion is recognized, i.e. processed and cleaved by the host cell, the MSP is secreted. Signals are selected based on the intended host cell, and may include bacterial yeast, mammalian and viral sequences. The native MSP signal or the herpes gD glycoprotein signal is suitable for use in mammalian expression systems.

Plasma proteins which have enhanced plasma half-life longer than that of soluble forms of MSPs having modified membrane anchor domain include serum albumin, immunoglobulins, apolipoproteins, and transferrin. Preferably, the MSP-plasma protein used for the fusion is not significantly immunogenic in the animal in which it is used (i.e., it is homologous to the therapeutic target) and the plasma protein does not cause undesirable side effects in patients by virtue of its normal biological activity.

In a specific embodiment the MSP extracellular domain is conjugated with an immunoglobulin constant region sequence. Immunoglobulins and certain variants thereof are known and many have been prepared in recombinant cell culture. For example, see U.S. Pat. No. 4,745,055; EP 256,654; Faulkner et al., Nature 298:286 (1982); EP 120, 694; EP 125,023; Morrison, J. Immun. 123:793 (1979); Köhler et al., P.N.A.S. USA 77:2197 (1980); Raso et al., Cancer Res. 41:2073 (1981); Morrison et al., Ann. Rev. Immunol. 2:239 (1984); Morrison, Science 229:1202 (1985); Morrison et al., P.N.A.S. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. See also Gascoigne et al., P.N.A.S. USA 84:2936–2940 (May, 1987), EP 325,224, and Thesis of Andrew Scott Peterson (Harvard University; degree awarded Nov. 22, 1988).

Ordinarily, the extracellular domains of MSPs are fused C-terminally to the N-terminus of the constant region of an immunoglobulin in place of the variable region(s) thereof, retaining at least functionally active hinge, CH2 and CH3 domains of the constant region of an immunoglobulin heavy chain. Two forms of such fusions are embraced herein. In one, the extracellular domains of two or more ordinarily membrane-bound MSP chains are fused N or C terminally to immunoglobulin constant regions (heterofusion), while in the other form only one chain of the MSP is fused to a constant region (monofusion). The heterofusions include fusions with either light or heavy chain constant regions, or both. The heterofusion is produced by transforming a host cell with DNA encoding the light chain fusions, the heavy chain fusions or both. For example, transfection with DNA encoding one MSP chain fused to a heavy chain constant region and the other MSP chain fused to a light chain constant region will result in heterotetramer or heterodimers bearing light and heavy chain fusions with MSP chains. These are not as desirable as monofusions since they are not as likely to be biologically active. Note that monofusions may contain more than one fused chain, but in these cases the MSP chain will always originate with the same subunit.

Monofusions are immunoglobulin variants in which one chain of an MSP is fused to a heavy or light chain (or constant domain thereof), while the remaining chain(s) of the MSP are not fused to an immunoglobulin but rather are associated with the fused chain in substantially the fashion as is normally the case with the native MSP. Typically, both the fused and unfused MSP chains in monofusions will be variants in which the membrane anchor domains are modified so as to not lodge in the membrane, most commonly where the membrane anchor domain of one MSP chain is deleted, and in the other the membrane anchor domain is deleted and then the remaining extracellular region fused at its N-terminus to the C-terminus of an immunoglobulin constant domain. The MSP chain or its fragment is fused to either a light chain or a heavy chain, but preferably a heavy chain. If the MSP only contained one membrane anchored chain then the remaining chain(s) will typically have their native sequence.

It may be desirable to produce mono-or polyfusions having immunoglobulin antigen binding capability as well as the capacity to bind the MSP ligand. Such products are made by transforming the host cells with DNA encoding light and heavy chain capable of binding an antigen (or are selected to already produce light chain) together with the light and/or heavy chain MSP fusion and the unfused MSP chain(s) (in the case of monofusions). This will yield constructs, for example, having the normal structures of immunoglobulins except that one or both light-heavy arms of the immunoglobulin will comprise a fusion with one chain of the MSP which in turn is assembled (covalently or noncovalently) with the remaining chain(s) of the MSP.

In those instances in which the fusion transformants also produce (or are transformed to produce) immunoglobulin chains not fused to an MSP subunit, the immunoglobulin variable domains may have unknown or known specificity for a given antigen. It is preferred that the host cells not be constitutively capable of making undetermined antibody, but rather that if they are to produce antibody that it be by transformation with DNA encoding a known immunoglobulin. Such immunoglobulins (which may include both heavy as well as light chains) exhibit specificity for a known antigen. Alternatively, these companion immunoglobulin chains will be devoid of functional variable or hypervariable domains (so as to be capable of multimer assembly but not antigen binding activity). For example, a product MSP fusion secreted and recoverable from host cells capable of expressing an intact heavy and light chain companion immunoglobulin will bear an antigen binding functionality as well as an MSP functionality. Such products will facilitate the crosslinking of MSP ligand with any desired antigen. Host cells may make more than one immunoglobulin product in such multiple transformations, and accordingly it may be necessary to recover one multimer form from another. This, however, will be a routine matter requiring separation on a gel or other chromatographic procedure, or by affinity chromatography based on the MSP ligand, the antigen or both.

Other proteins having extended plasma half life are fused to the MSP in similar fashion, except that instead of an immunoglobulin chain a transferrin, albumin, apolipoprotein or other sequence is employed. Monofusions are preferred when MSP chains are fused to single chain plasma proteins which do not ordinarily assemble into multimers.

The boundary for an MSP extracellular domain generally is at, or within about 20 residues N-terminal from, the N-terminus of the membrane anchor domain, and are readily identified from an inspection of the MSP sequence. It is not necessary to use the entire MSP extracellular domain, however, since smaller segments are commonly found to be adequate for ligand binding. Such segments are routinely identified by making deletional mutants or enzymatic digests and screening for ligand binding to identify active fragments, and fall within the scope of the term "MSP".

The MSP extracellular domain generally is fused at its C-terminus to the N-terminus of the immunoglobulin constant region or other stable plasma protein. The precise site at which the fusion is made is not critical; other sites neighboring or within the extracellular region or C-terminal to the mature N-terminus of the plasma protein may be selected in order to optimize the secretion or binding characteristics of the soluble MSP. The optimal site will be determined by routine experimentation.

Exemplary hetero-and chimeric MSP-immunoglobulin variants produced in accordance with this invention are schematically diagrammed below. "A" means at least a portion of the extracellular domain of an MSP containing its ligand binding site; $A_1$, $A_2$, $A_3$, etc. represent individual subunit chains of A; $V_L$, $V_H$, $C_L$ and $C_B$ represent light or heavy chain variable or constant domains of an immunoglobulin; n is an integer; and Y designates a covalent cross-linking moiety.

(a) $AC_L$;

(b) $AC_L-AC_L$;

(c) $AC_H-[AC_H,\ AC_L-AC_H,\ AC_L-V_HC_H,\ V_LC_L-AC_H$, or $V_LC_L-V_HC_H]$;

(d) $AC_L-AC_H-[AC_H,\ AC_L-AC_H,\ AC_L-V_HC_H,\ V_LC_L-AC_H$, or $V_LC_L-V_HC_H]$;

(e) $AC_L-V_HC_H-[AC_H,\ AC_L-AC_H,\ AC_L-V_HC_H,\ V_LC_L-AC_H$, or $V_LC_L-V_HC_H]$;

(f) $V_LC_L-AC_H-[AC_H,\ AC_L-AC_H,\ AC_L-V_HC_H,\ V_LC_L-AC_H$, or $V_LC_L-V_HC_H]$; or (g) $[A-Y]_n-[V_LC_L-V_HC_H]_2$.

The structures shown in this table show only key features, e.g. they do not show disulfide bonds. These are omitted in the interests of brevity. However, where such domains are required for binding activity they shall be construed as being present in the ordinary locations which they occupy in the immunoglobulin domain. These examples are representative of divalent antibodies; more complex structures would result by employing immunoglobulin heavy chain sequences from other classes, e.g. IgM. The immunoglobulin $V_L V_H$ antibody combining site, also designated as the companion immunoglobulin, preferably is capable of binding to a predetermined antigen.

Exemplary immunoglobulin constructs are described schematically below. Vertical lines indicate a noncovalent or covalent associative relationship.

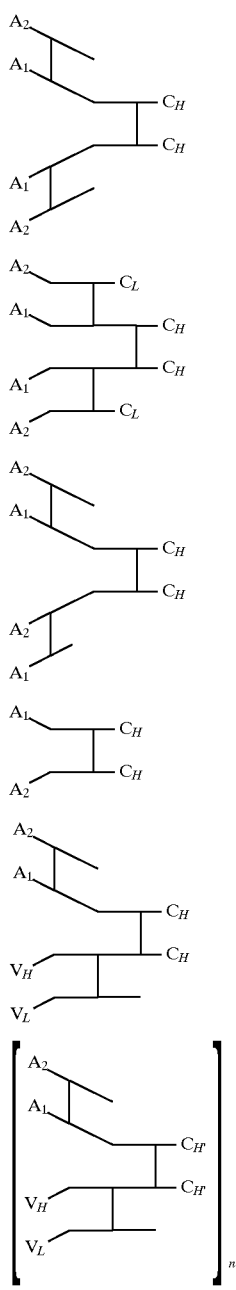

(h)

(i)

(j)

(k)

(l)

(m)

where n = 5 and $C_{H'}$ is the secreted heavy chain of IgM

-continued (n)

(o)

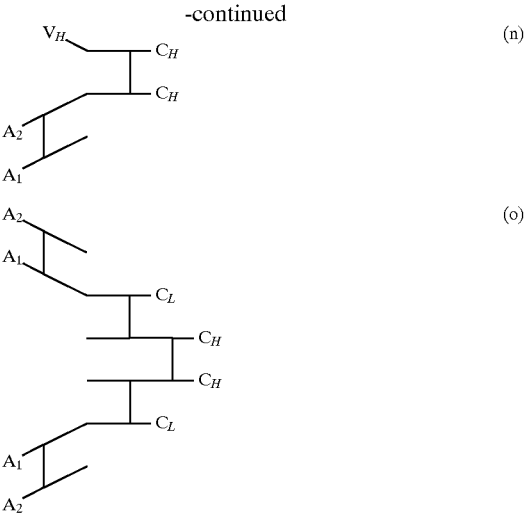

In product "(o)" the $C_H$ V domains have been deleted.

Suitable companion immunoglobulin combining sites and fusion partners are obtained from human IgG-1, -2, -3, or -4 subtypes, IgA, IgE, IgD or IgM, but preferably IgG-1. It is preferred to use the soluble form of IgM, or one in which the IgM membrane anchor domain has been modified so that it no longer lodges in the membrane.

A preferred embodiment is a fusion of an N-terminal portion of an MSP with a sequence beginning in the hinge region just upstream of the papain cleavage site which defines IgG $F_c$ chemically (residue 216, taking the first residue of heavy chain constant region to be 114 [Kabat et al., "Sequences of Proteins of Immunological Interest" 4th Ed., 1987], or analogous sites of other immunoglobulins).

The immunoglobulin or other plasma-stable polypeptide is fused to the C-termini of one or more of the MSP subunits, typically in place of at least one transmembrane and cytoplasmic domain of an MSP chain, although ordinarily only one of the subunits is substituted. In the case of GPIIb-IIIa this would be the beta subunit. The immunoglobulin domain such as a heavy chain also can be associated in normal fashion with a truncated or intact immunoglobulin heavy chain.

Variants in which an MSP extracellular domain is substituted for the variable region of an immunoglobulin chain are believed to exhibit improved in vivo plasma half life. These chimeras are constructed in a fashion similar to chimeric antibodies in which a variable domain from an antibody of one species is substituted for the variable domain of another species. See, for example, EP 0 125 023; Munro, Nature 312: (13 Dec. 1984); Neuberger et al., Nature 312: (13 Dec. 1984); Sharon et al., Nature 309: (24 May 1984); Morrison et al., Proc. Natl. Acad. Sci. USA 81:6851–6855 (1984); Morrison et al. Science 229:1202–1207 (1985); and Boulianne et al., Nature 312:643–646 (13 Dec. 1984). The DNA encoding the MSP extracellular domain is cleaved by a restriction enzyme at or proximal to the 3' end of the DNA encoding the domain and at a point at or near the DNA encoding the N-terminal end of the mature MSP polypeptide (where use of a different leader is contemplated) or at or proximal to the N-terminal coding region for the MSP (where the native MSP signal is employed). This DNA fragment then is readily inserted into DNA encoding e.g. an immunoglobulin light or heavy chain constant region and, if necessary, tailored by deletional mutagenesis. Preferably, this is a human immunoglobulin. DNA encoding immunoglobulin light or heavy chain constant regions is known or readily available from cDNA libraries or is synthesized. See for example, Adams et al., Biochemistry 19:2711–2719 (1980); Gough et al., Biochemistry 19:2702–2710 (1980); Dolby et al., P.N.A.S. USA, 77:6027–6031 (1980); Rice et al., P.N.A.S. USA 79:7862–7865 (1982); Falkner et al., Nature 298:286–288 (1982); and Morrison et al., Ann. Rev. Immunol. 2:239–256 (1984).

DNA encoding the chimeric chain(s) is transfected into a host cell for expression. If the host cell is producing an immunoglobulin prior to transfection then one need only transfect with the MSP fused to light or to heavy chain to produce a heteroantibody. The aforementioned immunoglobulins having one or more arms bearing the MSP domain and one or more arms bearing companion variable regions result in dual specificity for MSP ligand and for an antigen. These are produced by the above-described recombinant methods or by in vitro procedures. In the latter case, for example, F(ab')$_2$ fragments of the MSP fusion and an immunoglobulin are prepared, the F(ab')2 fragments converted to Fab' fragments by reduction under mild reducing conditions, and then reoxidized in each other's presence under acidic conditions in accord with methods known per se. See also U.S. Pat. No. 4,444,878.

Additionally, procedures are known for producing intact heteroantibodies from immunoglobulins having different specificities. These procedures are adopted for the in vitro production of heterochimeric antibodies by simply substituting the MSP fusions for one of the previously employed immunoglobulins.

In an alternative method for producing a heterofunctional antibody, host cells producing an MSP-immunoglobulin fusion, e.g. transfected myelomas, also are fused with B cells or hybridomas which secrete antibody having the desired companion specificity for an antigen. Heterobifunctional antibody is recovered from the culture medium of such hybridomas, and thus may be produced somewhat more conveniently than by conventional in vitro resorting methods (EP 68,763).

Another class of MSP variants are deletional variants. Deletions are characterized by the removal of one or more amino acid residues from an MSP sequence. Typically, the membrane anchor and cytoplasmic domains of all MSP subunits are deleted. However, any other suitable site N-terminal to the transmembrane which preserves the matrix protein or ligand-binding capability of the MSP is suitable. Excluded from the scope of deletional variants are the protein digestion fragments that may have heretofore been obtained in the course of elucidating amino acid sequences of MSPs.

Substitutional variants are those in which at least one residue in the MSP sequence has been removed and a different residue inserted in its place. Table 1 below describes substitutions which in general will result in fine modulation of the characteristics of an MSP.

TABLE 1

| Original Residue | Exemplary Substitutions |
| --- | --- |
| Ala | ser |
| Arg | lys |
| Asn | gln; his |
| Asp | glu |
| Cys | ser; ala |
| Gln | asn |
| Glu | asp |
| Gly | pro |
| His | asn; gln |

TABLE 1-continued

| Original Residue | Exemplary Substitutions |
| --- | --- |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in MSP properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

A preferred class of substitutional or deletional variants are those involving a membrane anchor region of the MSP. Transmembrane regions of MSP subunits are highly hydrophobic or lipophilic domains that are the proper size to span the lipid bilayer of the cellular membrane. They are believed to anchor the MSP in the cell membrane. Other cell surface molecules are anchored by lipid modification, as by phospholipid anchors.

Deletion or substitution of the membrane anchor domain will facilitate recovery and provide a soluble form of the MSP by reducing its cellular or membrane lipid affinity and improving its water solubility. If the membrane anchor domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of the membrane anchor domain-deleted MSP is that it is secreted into the culture medium of recombinant hosts. This variant is soluble in body fluids such as blood and does not have an appreciable affinity for cell membrane lipids, thus considerably simplifying its recovery from recombinant cell culture. Surprisingly, MSPs in which membrane inserted chains have been modified so as to be no longer capable of stable insertion into cell membranes are capable of proper association and secretion from recombinant host cells even if the MSP chains are not fused to a multimer-forming sequence such as an immunoglobulin. A multimer-forming sequence is a multichain polypeptide that contains that portion of a multiple chain polypeptide that, when in the unfused form in nature, forms covalently or noncovalently associated multiple chain structures.

It will be amply apparent from the foregoing discussion that substitutions, deletions, insertions or any combination thereof are introduced to arrive at a final construct. None of the variants will have a functional membrane anchor domain and preferably will not have a functional cytoplasmic sequence. This is generally accomplished by deletion of the relevant domain, although adequate insertional or substitutional variants also are effective for this purpose. For example, the transmembrane domain is substituted by any amino acid sequence, e.g. a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) MSPs, these variants are secreted into the culture medium of recombinant hosts.

MSP variants are prepared conveniently by site specific mutagenesis of nucleotides in the DNA encoding the MSP, thereby producing DNA encoding the variant, and thereafter expressing the DNA in recombinant cell culture. Obviously, changes in the DNA encoding the variant MSPs must not place the sequence out of reading frame and preferably will not create complementary regions that could produce secondary mRNA structure deleterious to expression (EP 75,444A). The MSP variants typically exhibit the same matrix or ligand binding activity as does the naturally-occurring prototype, although variants also are selected in order to modify the characteristics of the MSP as indicated above.

While the site for introducing an amino acid sequence variation is predetermined, the mutation per se need not be predetermined. For example, in order to optimize the performance of a mutation at a given site, random or saturation mutagenesis (where all 20 possible residues are inserted) may be conducted at the target codon or region and the expressed MSP variants screened for the optimal combination of desired activities.

MSP variants that are not capable of binding to their matrix proteins or ligands are useful nonetheless as immunogens for raising antibodies to the MSP or as immunoassay kit components (labelled, as a competitive reagent for native MSP, or unlabelled as a standard for an MSP assay) so long as at least one MSP epitope remains active.

Contemplated herein are MSPs or MSP amino acid sequence or glycosylation variants (including those already described above) wherein one or more MSP subunits are conjugated with a nonproteinaceous polymer. It will be understood that the nonproteinaceous polymer which is conjugated to MSP excludes oligosaccharides that are present in the same positions in the native or starting MSP, i.e. the polymer is extraneous or heterologous to the MSP.

It is within the scope hereof to move, add or delete glycosylation sites by site-directed mutagenesis of MSP polypeptide in order to increase the number of or change the location of the carbohydrate substituents. The nature of the carbohydrate is modified in conventional fashion by in vitro enzymatic digestion or by selecting host cells that affix the selected carbohydrate (or do not glycosylate at all).

The nonproteinaceous polymer ordinarily is a hydrophilic synthetic polymer, i.e., a polymer not otherwise found in nature. However, polymers which exist in nature and are produced by recombinant or methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; and heparin. Where the polysaccharide is the native glycosylation or the glycosylation attendant on recombinant expression of MSP, the site of substitution ordinarily is located at other than an N or O-linked glycosylation site of the MSP or the MSP variant is an amino acid sequence variant in which an additional or substitute N or O-linked site has been introduced into the molecule.

Mixtures of such polymers are employed, or the polymer may be homogeneous. The polymer prior to crosslinking need not be, but preferably is, water soluble, but the final conjugate must be soluble in biological fluids such as blood. In addition, for therapeutic uses the polymer should not be highly immunogenic when conjugated to the MSP, nor should it possess viscosity that is incompatible with intravenous infusion or injection if it is intended to be administered by such routes.

Preferably the polymer contains only a single group which is reactive with MSP. This helps to avoid crosslinking of MSP molecules. However, it is within the scope herein to optimize reaction conditions to reduce crosslinking, or to purify the reaction products through gel filtration or chromatographic sieves to recover substantially homogeneous derivatives.

The molecular weight of the polymer ranges about from 100 to 500,000, and preferably is about from 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation. Ordinarily, the molecular weight of the MSP-polymer conjugate will exceed about 70,000 although molecules having lesser molecular weights are suitable.

The polymer generally is covalently linked to MSP through a multifunctional crosslinking agent which reacts with the polymer and one or more amino acid or sugar residues of MSP. However, it is within the scope of this invention to directly crosslink the polymer to the MSP by reacting a derivatized polymer with MSP, or vice versa.

A suitable MSP covalent crosslinking site is the N-terminal amino group and epsilon amino groups found on lysine residues, although other amino, imino, carboxyl, sulfydryl, hydroxyl or other hydrophilic groups serve as useful sites of substitution. The polymer may be covalently bonded directly to MSP without the use of a multifunctional (ordinarily bifunctional) crosslinking agent. Examples of such crosslinking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl) dithio] propioimidate yield photoactivatable intermediates which are capable of forming cross-links in the presence of light. Alternatively, reactive water soluble matrices such as cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for cross-linking the polymer and MSP. Covalent bonding to MSP amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Polymers are conjugated to the oligosaccharide substituents by chemical, e.g. metaperiodate, or enzymatic oxidation, e.g. glucose or galactose oxidase, (to produce the aldehyde derivative of the carbohydrate), followed by reaction with hydrazide or amino-derivatized polymers, in the same fashion as is described by Heitzmann et al., P.N.A.S., 71:3537–3541 (1974) or Bayer et al., Methods in Enzymology, 62:310 (1979), for the labeling of oligosaccharides with biotin or avidin. Further, other chemical or enzymatic methods which have been used heretofore to link oligosaccharides and polymers may be suitable. Substituted oligosaccharides are particularly advantageous since there are fewer carbohydrate substitutions than amino acid sites for derivatization, thus improving the stability, activity and homogeneity of the conjugate. Finally, the MSP oligosaccharide substituents are enzymatically modified to remove sugars, e.g. by neuraminidase digestion, as a final product or prior to polymer derivatization.

The polymer will bear a group which is directly reactive with an amino acid side chain, or the N- or C-terminus of MSP, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides to MSP.

"Water soluble" in reference to the starting polymer means that the polymer or its reactive intermediate used for conjugation is sufficiently water soluble to participate in a derivatization reaction with MSP.

The degree of substitution of MSP will vary depending upon the number of reactive sites on the protein, whether intact or truncated MSP is used, whether the MSP is a fusion with a protein heterologous to MSP, the molecular weight, hydrophilicity and other characteristics of the polymer, and the particular sites chosen. In general, the MSP portion of the conjugate is substituted with about from 1 to 10 polymer molecules, while any heterologous sequence which is fused to MSP may be substituted with an essentially unlimited number of polymer molecules so long as the activity of the MSP moiety is not significantly adversely affected. The optimal degree of crosslinking is easily determined by an experimental matrix in which the time, temperature and other reaction conditions are varied to change the degree of substitution, after which the ability of the conjugates to bind matrix protein or ligand is determined.

The polymer, e.g., PEG is crosslinked to MSP by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead to inactivation of proteins containing sulfhydryl groups. Carbonyl diimidazole chemistry (Beauchamp et al., "Anal. Biochem." 131:25–33 [1983]) requires high pH (>8.5), which can inactivate proteins. Moreover, since the "activated PEG" intermediate can react with water, a very large molar excess of "activated PEG" over protein is required. In general, aldehyde chemistry (Royer, U.S. Pat. No. 4,002,531) is preferred since it requires only a 40 fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., "J. Polym. Sci., Polym. Chem. Ed." 22:341–352 [1984]). Use of a moffatt oxidation, utilizing DMSO and acetic anhydride, obviates this problem. In addition, the sodium borohydride suggested by Royer must be used at a high pH and has a significant tendency to reduce disulphide bonds. In contrast, sodium cyanoborohydride, which is effective at neutral pH, has very little tendency to reduce disulphide bonds.

The MSP conjugates of this invention typically are separated from unreacted starting materials by gel filtration. Most conveniently, MSP conjugates are eluted from hydrophobic interaction chromatography medium, e.g. alkyl Sepharose, by the use of a decreasing salt gradient. This, as well as the gel filtration approach described above, resolves conjugates on the basis of the degree of substitution.

The DNA encoding an MSP is obtained by known procedures, in most instances by reference to publications describing DNA encoding the MSP. In general, prokaryotes are used for cloning of MSP variant DNA sequences. For example, a $\lambda$-resistant strain of E. coli JM 101 for propagating M13 phage; Messing et al., Nucl. Acids. Res. 9(2):309–321 [1981]); and E. coli K12 strain 294 (ATCC No. 31446) are particularly useful. Other microbial strains which may be used include E. coli B, or UM101. These examples are illustrative rather than limiting. Nucleic acid also is cloned using various well known in vitro amplification processes.

DNA encoding the variant MSPs are inserted for expression into vectors containing promoters and control sequences which are derived from species compatible with the intended host cell. The vector ordinarily, but need not, carry a replication site as well as one or more marker sequences which are capable of providing phenotypic selection in transformed cells. For example, E. coli is typically transformed using a derivative of pBR322 which is a plasmid derived from an E. coli species (Bolivar, et al., Gene 2: 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA constructions.

Promoters suitable for use with prokaryotic hosts illustratively include the $\mu$-lactamase and lactose promoter systems (Chang et al., Nature, 275: 615 [1978]; and Goeddel et al., Nature 281: 544 [1979]), alkaline phosphatase, the tryptophan (trp) promoter system (Goeddel, Nucleic Acids Res. 8: 4057 [1980] and EPO Appln. Publ. No. 36,776) and hybrid promoters such as the tac promoter (H. de Boer et al., Proc. Natl. Acad. Sci. USA 80: 21–25 [1983]). However, other functional bacterial promoters are suitable. Their nucleotide sequences are generally known, thereby enabling a skilled worker operably to ligate them to DNA encoding the MSP variant using linkers or adaptors to supply any required restriction sites (Siebenlist et al., Cell 20: 269 [1980]). Promoters for use in bacterial systems also will contain a Shine-Dalgarno (S.D.) sequence operably linked to the DNA encoding the antigen.

In addition to prokaryotes, eukaryotic microbes such as yeast cultures also are useful as cloning or expression hosts. *Saccharomyces cerevisiae*, or common baker's yeast is the most commonly used eukaryotic microorganism, although a number of other strains are commonly available. For expression in Saccharomyces, the plasmid YRp7, for example, (Stinchcomb, et al., Nature 282: 39 [1979]; Kingsman et al, Gene 7: 141 [1979]; Tschemper et al., Gene 10: 157 [1980]) is commonly used. This plasmid already contains the trp1 gene which provides a selection marker for a mutant strain of yeast lacking the ability to grow in tryptophan, for example ATCC no. 44076 or PEP4-1 (Jones, Genetics 85: 12 [1977]). The presence of the trp1 lesion as a characteristic of the yeast host cell genome then provides an effective means of selection by growth in the absence of tryptophan.

Suitable promoting sequences for use with yeast hosts include the promoters for 3-phosphoglycerate kinase (Hitzeman et al., J. Biol. Chem. 255: 2073 [1980]) or other glycolytic enzymes (Hess et al., J. Adv. Enzyme Reg. 7: 149 [1968]; and Holland, Biochemistry 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Pat. No. Publication No. 73,657A. Yeast enhancers also are advantageously used with yeast promoters.

Promoters for controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters, e.g. the beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful.

DNA transcription in higher eukaryotes is increased by inserting an enhancer sequence into the vector. Enhancers are cis-acting elements of DNA, usually from about 10 to 300 bp, that act to increase the transcription initiation capability of a promoter. Enhancers are relatively orientation and position independent having been found 5' (Laimins, L. et al., Proc.Natl.Acad.Sci. 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding the MSP.

Expression vector systems generally will contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented medium. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which is inactivated by DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred host cells for expressing the MSP variants of this invention are mammalian host-vector systems, examples of suitable hosts including: monkey kidney CV1 line transformed by SV40 (COS-7, ATCC CRL, 1651); human embryonic kidney line (293, Graham, F. L. et al., J. Gen Virol. 36: 59 [1977] and 293S cells, either of which are equally satisfactory); baby hamster kidney cells (BHK, ATCC CCL 10); chinese hamster ovary-cells DHFR (CHO, Urlaub and Chasin, Proc.Natl.Acad.Sci. (USA) 77: 4216 [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51 cells); and TRI cells (Mather, J. P. et al., Annals N.Y. Acad. Sci. 383: 44–68 [1982]).

"Transformation" means introducing DNA into an organism so that the DNA is replicable, either as an extrachromosomal element or by chromosomal integration. One suitable for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell walls are used as hosts, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard and manipulative ligation techniques. Isolated plasmids or DNA fragments are cleaved, tailored, and relegated in the form desired to form the plasmids required. Suitable procedures are well known for the construction described herein. See, for example, (Maniatis, T. et al., *Molecular Cloning*, 133–134 Cold Spring Harbor, [1982]; "Current Protocols in Molecular Biology", edited by Ausubel et al., [1987], pub. by Greene Publishing Associates & Wiley-Interscience).

Ordinarily, DNA encoding each subunit of a given MSP (or transmembrane modified variant) is simultaneously cotransfected into the host cell, although such transfections can be done sequentially. MSP variants in which one subunit is exchanged for the analogous subunit of another MSP (to produce heterologous heterodimers) are produced by cotransforming a recombinant host (typically mammalian cell) with each of the heterologous subunits, for example, exchanging the fibronectin α subunit for the a subunit of GPIIb-IIIa (an a subunit exchange), or the fibronectin β subunit for the β subunit of GPIIb-IIIa (a β subunit exchange).

Correct plasmid sequences are confirmed by transforming *E. coli* K12 strain 294 (ATCC 31446) with ligation mixtures, successful transformants selected by ampicillin or tetracycline resistance where appropriate, plasmids from the transformants prepared, and then analyzed by restriction enzyme digestion and/or sequenced by the method of Messing et al., Nucleic Acids Res. 9: 309 (1981) or by the method of Maxam et al., Methods in Enzymology 65: 499 (1980).

Host cells are transformed with the expression vectors of this invention. Thereafter they are cultured in appropriate culture media, e.g. containing substances for inducing promoters, selecting transformants or amplifying genes. The culture conditions, such as temperature, pH and the like, are those previously used with the host cell selected for expression, and will be apparent to the ordinarily skilled artisan. For expression of GPIIb-IIIa it is preferable that the culture medium contain calcium and magnesium salts since divalent cations are needed to enhance the stability of secreted GPIIb-IIIa and other calcium dependent MSPs.

The secreted MSP variants are recovered and purified from the culture supernatants or lysates of recombinant hosts. Typically, the supernatants are concentrated by ultrafiltration, contacted with a ligand (e.g. RGD) or matrix protein affinity or immunoaffinity resin so as to adsorb the MSP variant, and eluted from the adsorbent Optionally, the MSP is purified by HPLC, lectin columns, gel exclusion, hydrophobic interaction or ion exchange chromatography.

The purified MSP is formulated into conventional pharmacologically acceptable excipients.

The soluble MSP variants of this invention are useful in therapeutics, diagnostics and preparative procedures. In diagnostics, the soluble MSPs are employed in place of membrane extracts as standards or controls, or are labelled with a radioisotope or other detectable group for use in competitive-type radioimmuno- or radioreceptor assays for the MSP or its antibodies.

The soluble MSPs are crosslinked to insoluble supports by the methods described herein and employed for the purification of their ligands or matrix proteins, e.g. fibronectin, fibrinogen and the like. Alternatively, the soluble MSPs are used to adsorb ligand or matrix protein in solution, followed by precipitation by antisera, ammonium sulfate or the like in order to recover the ligand or matrix protein complex. The complex is then dissociated by HPLC, electrophoresis, gel chromatography or other conventional methods.

Therapeutic uses of soluble MSPs will be a function of the biological activity of each MSP, and will be apparent therefrom. The soluble MSP variants herein may act as agonists or antagonists of the corresponding native, membrane-bound receptors. The soluble GPIIb-IIIa receptor, for example, is useful as an anticoagulant and for the treatment of disorders associated with platelet aggregation, particularly in the prevention of reocclusion following thrombolytic therapy. Soluble matrix receptors, especially soluble GPIIb-IIIa, also are useful as antagonists to matrix-adhesion dependent neoplastic metastasis. Soluble LFA-1 variants are an antagonist of T-lymphocyte function, thereby being efficacious as immunosuppressive or anti-inflammatory agents, particularly in reperfusion injury. Soluble Mac-1 variants may find use in the treatment of complement activation disorders.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide or agarose gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103–6114 [1981], and Goeddel, D. et al., Nucleic Acids Res. 8: 4057 [1980]).

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 μg of approximately equimolar amounts of the DNA fragments to be ligated.

The following examples merely illustrate the best mode now contemplated for practicing the invention, but should not be construed to limit the invention. All literature citations herein are expressly incorporated by reference.

EXAMPLE 1

Cloning of Glycoprotein IIb (GPIIb) cDNA

Messenger RNA was prepared from cultured human erythroleukemia cells (HEL, ATCC TIB 180). An oligo(dT)-primed cDNA library was prepared using this mRNA in the bacteriophage lambda ZAP (Stratagene Cloning Systems). The lambda ZAP library was screened with a 45-mer oligonucleotide (2b1) derived from the 5' end of the published cDNA sequence for GPIIb from HEL cells (Poncz et al., "J. Biol. Chem." 262(18):8476–8482 [1987]). Several positively-hybridizing phage were purified, and the cDNA inserts they contained were subjected to restriction enzyme digestion analysis. From these results a phage which appeared to contain a full-length coding insert for GPIIb was selected for further analysis. DNA sequencing of this phage insert DNA gave over 300 bases which corresponded exactly with the published cDNA sequence from the 5' end of the mRNA (Poncz et al.) except having 4 additional bases on its 5' end. The cDNA insert was digested with EcoRI (this site being derived from the linkers ligated to the ends of the cDNAs during production of the library) and HindIII, which cuts the GPIIb insert uniquely downstream of the end of the coding sequence. This EcoRI to HindIII restriction fragment, containing the entire coding region for GPIIb was ligated into mammalian cell expression vector pRK5 (U.S. Ser. No. 07/097,472) which had been digested with EcoRI and HindIII, and expression vector GPIIb-pRK5 was recovered.

Construction of Full-Length Glycoprotein IIIa (GPIIIa) cDNA

A cDNA clone for GPIIIa, incomplete at its 5' end, was obtained (Rosa et al., "Blood" 72(2):593 [1988]). The cDNA was provided as an EcoRI (site derived from the cDNA library construction linker) to PstI (site downstream of the end of the coding sequence) insert in the plasmid vector pIBI20 (International Biotechnologies, Inc.) This plasmid was digested with HindIII to cut the plasmid at the unique HindIII site in pIBI20 downstream of the terminal PstI site in the cDNA insert, and incompletely with ApaI, to give a cDNA fragment bounded by the ApaI site at the 5' end of the sequence and HindIII from the plasmid. vector. The relevant domain for the construction is shown below.

```
        -7                        -1  1                            6
        L    A    G    V    G    V   G    G    P    N    I    C    T
...    CTG  GCG  GGC  GTT  GGC  GTA  GGA  GGG  CCC  AAC  ATC  TGT  ACC ...
...    GAC  CGC  CCG  CAA  CCG  CAT  CCT  CCC  GGG  TTG  TAG  ACA  TGG ...
       EcoRI                           ApaI                        HindIII
```

Synthetic complementary oligonucleotides were used to reconstruct a full-length coding construct for GPIIIa based on the published cloned cDNA sequence (Fitzgerald et al., "J. Biol. Chem." 262(9):3936 [1987]). The oligonucleotide sequence, ending in ApaI, was ligated to the ApaI site of the above ApaI-HindIII fragment, to give a DNA fragment now bounded by EcoRI and HindIII. This EcoRI to HindIII fragment, containing the entire coding region for GPIIIa was ligated into pRK5 which had been digested with EcoRI and HindIII, and expression vector GPIIIa-pRK5 was recovered. The relevant oligonucleotide sequences are shown below.

```
                          -26
                          M    R    A    R    P    R    P    R    P    L    W
        AAT  TCT  AGA  GCC  GCC  ATG  AGA  GCA  CGT  CCT  CGA  CCA  CGT  CCT  CTC  TGG —
             GA   TCT  CGG  CGG  TAC  TCT  CGT  GCA  GGA  GCT  GGT  GCA  GGA  GAG  ACC —
        EcoRI
             XbaI
                                                                              -1   1
        A    T    V    L    A    L    G    A    L    A    G    V    G    V   G    G    P
```

```
GCG  ACT  GTG  CTG  GCA  CTG  GGA  GCA  CTG  GCT  GGT  GTT  GGA  GTA  GGA  GGG  CC
CGC  TGA  CAC  GAC  CGT  GAC  CCT  CGT  GAC  CGA  CCA  CAA  CCT  CAT  CCT  C
                                                                       ApaI
```

The synthetic oligonucleotides were designed such that the amino acids encoded were identical to those predicted from the published cloned cDNAs (Fitzgerald et al., Rosa et al.), but the codons were not always identical with the naturally-occurring cloned cDNA. FIG. 3 compares the coding strands of the synthetic and natural sequences. Asterisks between each sequence indicate which nucleotides are identical. These changes were introduced for three reasons.

1. In light of difficulties encountered in sequencing the cDNA, we concluded that the cDNA could contain secondary structure adverse to translational efficiency. To minimize possible secondary structure in the mRNA produced from expression constructs, the percentage of G and C bases in the natural coding sequence was lessened by changing some codons to others which had a lower G and/or C content, but which coded for the same amino acid. These altered codons were chosen such that only codons used frequently in the remainder of the cDNA were substituted. Karnick et al., "J. Biol. Chem." 2(5) :9255 (1987); Devlin et al., "Gene" 65:13 (1988).
2. The codon for arginine (R, amino acid -25), immediately following the initiator methionine codon (M -26), was changed from CGA to AGA. Kozak, "Nucl. Acids Res." 15(20):8125 [1987] and Kozak, "J. Mol. Biol." 196:947 [1987].
3. The DNA sequence upstream of the initiator methionine codon was not based on the natural DNA sequence. The synthetic complementary oligonucleotides were such that an EcoRI site was present at one end, followed by an XbaI recognition sequence, and then followed by a GCC GCC motif immediately upstream of the initiator methionine. Kozak, "J. Mol. Biol." Id.

The plasmids encoding GPIIb and GPIIIa (GPIIb-pRK5 and GPIIIa-pRK5) were transfected in 293S cells and cultured under conventional conditions for transient expression as described below. The cells were harvested and analyzed for GPIIb-IIIa expression. Expression was confirmed by the presence of correctly sized bands on a Western gel, immunologically visualized by FACS sorting, and immunoprecipitation of intact cells labeled metabolically with $S^{35}$ or by $^{125}I$ surface-labelling.

EXAMPLE 2

Construction of cDNA Encoding Truncated GPIIb

The starting point for the construction of the GPIIb truncated form was the full-length coding construction for GPIIb described in Example 1. The relevant domain for this construction is shown below.

```
                                       putative transmembrane
                                              region
                                               962
      L    R    A    L    E    E    R    A    I
...  CTC  CGG  GCC  TTG  GAG  GAC  AGG  GCC  ATT  ...
...  GAG  GCC  CGG  AAC  CTC  CTC  TCC  CGG  TAA  ...
EcoRI      StyI
```

The DNA fragment from the EcoRI site (upstream of the initiator ATG codon) to the StyI site indicated above was isolated and ligated to complementary synthetic oligonucleotides such that the DNA sequence thus obtained coded for the natural GPIIb sequence up to amino acid residue 962 (arginine) and was then followed by a TGA stop codon.

```
A    L    E    E    R    Stop
C   TTG  GAG  GAG  AGG  TGA  TGA  A
         CTC  CTC  TCC  ACT  ACT  TTC  GA
StyI                                HindIII
```

In the natural sequence, arginine 962 is followed by an approximately 26 amino acid putative hydrophobic transmembrane domain and a cytoplasmic domain (Poncz et al.). Thus, in this construction both of these domains have been deleted from the coding region of the construction. The end of the synthetic fragment terminated in a HindIII restriction site. The entire DNA fragment bounded by EcoRI and HindIII restriction sites was ligated into pRK5 which had been digested with EcoRI and HindIII. Expression vector GPIIbtrunc-pRK5 was recovered.

The EcoRI to HindIII fragment outlined above was rescued from GPIIbtrunc-pRK5 and subjected to analysis by DNA sequencing. Over 250 bases from each end of the insert were sequenced and corresponded exactly to that which was predicted.

Construction of cDNA Encoding Truncated GPIIIa

The starting point for the construction of the GPIIIa truncated form was the full-length coding construction for GPIIIa described in Example 1. The relevant domain for this construction is shown below.

```
                                    putative transmembrane region
                                              962
      P    K    G    P    D    I    L    L
...  CCC  AAG  GGC  CCT  GAC  ATC  CTG  GTG  ...
...  GGG  TTC  CCG  GGA  CTG  TAG  GAC  CAC  ...
XbaI           ApaI
```

The DNA fragment from the XbaI site (upstream of the initiator ATG codon) to the ApaI site indicated below was isolated and ligated to complementary synthetic oligonucleotides such that the DNA sequence thus obtained coded for the natural GPIIIa sequence up to amino acid residue 692 (aspartic acid) and was then followed by a TGA stop codon.

```
G    P    D    Stop
    CT   GAC  TGA  TGA  GAT  CTA
CCG  GGA  CTG  ACT  ACT  CTA  GAT  TCG  A
ApaI                                HindIII
```

In the natural sequence, aspartic acid 692 is followed by an approximately 29 amino acid putative hydrophobic transmembrane domain and a cytoplasmic domain (Fitzgerald et al.) Thus, in this construction both of these domains have been deleted from the coding region of the construction. The end of the synthetic fragment terminated in a HindIII restriction site. The entire fragment bounded by XbaI and HindIII restriction sites, was ligated into pRK5 previously digested with XbaI and HindIII and trunc expression vector GPIIIatrunc-pRK5 was recovered.

The XbaI to HindIII fragment outlined above was rescued front GPIIatrunc-pRK5, and subjected to analysis by DNA sequencing. Over 200 bases from each end of the insert were sequenced and corresponded exactly to that which was predicted.

Expression of Truncated Human GPIIb-IIIa Receptor in a Eukaryotic Host:

Human embryonic kidney cells (293S) were cotransfected with the expression vectors GPIIbtrunc-pRK5 and GPIIIatrunc-pRK5 using CaPO$_4$ (Graham et al., "Virology" 52:456 [1973]) using the host system described in EP 260,148.

Transient Expression

High levels of transient expression were obtained when 293S cells were cotransfected with GPIIbtrunc-pRK5, GPIIIatrunc-pRK5 and adenovirus VA RNA-DNA (U.S. Ser. No. 07/101,712; Akusjarvietal, "Mol. Cell. Biol." 7:549 [1987]) and grown in standard growth media (50% Dulbeccos Modified Eagle Media, 50% F12 mixture, 2 mM L-glutamine and 10% fetal bovine serum). 16 hours after glycerol shock cells were transferred to serum free media (Dulbeccos Modified Eagle Media, 0.1% glucose, 10 µg/ml insulin) and grown for a further 48 hours, at which time cells and culture media were harvested. Conditioned cell culture fluid was centrifuged to remove contaminating cell debris and then quick frozen in dry ice-ethanol and stored at −70° C. until analyzed. Cells were removed from 6 cm plates by suspension in 0.6 ml of 150 mM NaCl, 10 mM Tris (pH 7.5), 1% Triton X-100, 2 mM PMSF, 0.5 µg/ml leupeptin and 2 µg/ml pepstatin A followed by extraction for 30 minutes on ice with vortexing. Cellular debris was removed by centrifugation at 10,000 g and samples stored at −70° C. The soluble GPIIb-IIIa was recovered by Q-Sepharose (fast-flow) chromatography with 10 column volumes of 20 mM MES buffer/1 mM CaCl$_2$ pH 6.5 and gradient elution over 0–400 mM NaCl. The peak soluble GPIIb-IIIa tended to elute at about 200–250 mM NaCl. The eluate was concentrated to 3% of the column volume of an S-300 column, after which the concentrate was exclusion chromatographed on the a-350 column using 10 mM Tris/150mM NaCl/1 mM CaCl$_2$ pH 7.5. Some of the full length GPIIb transfected into 293S cells associated with endogenous $\alpha_V$. The secretion of soluble GPIIb with soluble GPIIIa avoided the need to purify BPIIb-IIIa from the $\alpha_V B_3$ vitronectin receptor, as would have been the case if the full length subunits had been used. See Bodary et al., J. Biol. Chem. 32:18859 (Nov. 15, 1989).

Stable Expression

Stable 293S clones expressing truncated GPIIb-IIIa were established by co-transfection of GPIIbtrunc-pRK5 and GPIIIatrunc-pRK5 with pRSVneo (Gorman et al., "Science" 221:551–552 [1983]). Forty eight hours after transfection cells were passaged into standard growth media containing 800 µg/ml of G418. Two weeks later, G418 resistant clone were picked and grown in standard growth media containing 400 µg/ml of G418. Clones were grown for 48 hours in serum free medium and the conditioned culture medium assayed for the expression of secreted forms of GPIIb-IIIa by Western blot analysis.

Analysis of Expressed Truncated GPIIb-IIIa

Transiently transfected cells were assayed for expression by pulse-chase analysis followed by immunoprecipitation using a panel of monoclonal antibodies generated against purified platelet GPIIb-IIIa. S$^{35}$-cysteine and -methionine metabolically labeled proteins were recovered from the culture fluid of cells cotransfected with both GPIIbtrunc-pRK5 and GPIIIatrunc-pRK5 as described above. Truncated GPIIb-IIIa was immunoprecipitated from cell culture fluid with a panel of mouse monoclonal antibodies (AP2 [Montgomery et al., "J. Clin. Invest." 71:385 (1983)], 2D2, 3A8, 4B12, and AP3 [Newman et al., "Blood" 65:227 (1985)]) by incubation with Protein A Sepharose CL4B (Pharmacia), bound to rabbit IgG antibodies directed against mouse IgG. Electrophoresis of the immunoprecipitated proteins demonstrated the secretion of recombinant truncated GPIIb-IIIa whose size was in agreement with the molecular weights expected of the modified cDNAs. Monoclonal antibodies specific to the GPIIb-IIIa complex (AP2), GPIIb (2D2, 3A8) and GPIIIa (4B12, AP3) all immunoprecipitate both the GPIIb and GPIIIa truncated proteins, demonstrating that the recombinant secreted proteins are present in the form of a complex. Cells which received no DNA or the GPIIbtrunc-pRK5 alone or GPIIIatrunc-pRK5 alone do not secrete proteins at levels which are detectable by monoclonal antibodies to GPIIb or GPIIIa.

The expression of individual subunits of GPIIb or GPIIIa in transiently transfected cells was demonstrated using Western blot analysis. Cells were extracted as described above and culture media (recovered as above) were concentrated 2-fold by ultrafiltration and analyzed by electrophoresis on polyacrylamide gels (Laemmli, U. K., "Nature" 227:680–685 [1970]) and by Western Blotting (Towbin et al., Proc.Natl.Acad.Sci.USA 76:4350–4354 [1979]). Mouse monoclonal antibodies specific for GPIIb and GPIIIa were used in this analysis. Horse radish peroxidase-conjugated antibodies directed against the murine monoclonals were used to visualize the individual GPIIbtrunc and GPIIIatrunc proteins in the extracts.

The stable clones expressing the GPIIb-IIIa truncated constructs were shown to secrete the recombinant proteins of the expected sizes using Western blot analysis.

That the GPIIb-IIIa trunc proteins secreted from stable clones were present as a complex was demonstrated by their detection, after direct transfer of culture medium to nitrocellulose by aspiration, with monoclonal antibody AP2.

The truncated GPIIb or GPIIIa proteins were not detected in culture media when expressed as individual subunits: either they are not secreted or the efficiency of secretion is reduced to levels which preclude detection by immunoprecipitation or by Western blot analysis.

EXAMPLE 3

Demonstration of Fibrinogen Binding of Secreted Human GPIIb-IIIa Polypeptide Complex The functional activity of the secreted truncated GPIIb-IIIa is; shown by its specific absorption to an affinity matrix containing the natural ligand, fibrinogen, for the GPIIb-IIIa receptor.

A stable clone from Example 2 which was expressing the GPIIb-IIIa truncated polypeptide complex was grown for 20 hours under serum free conditions (DMEM culture medium, 0.1% glucose, 10 µg/ml insulin, 1.5 µg/ml L-cysteine, 2.4 µg/ml L-methionine, 200 µCi/ml S$^{35}$ methionine and 200 µCi/ml S$^{35}$ cysteine). The conditioned cell culture fluid was first concentrated by ultrafiltration then purified by fibrinogen affinity chromatography. The fibrinogen affinity column was produced by coupling highly purified human fibrinogen to CNBr-activated Sepharose 4B (Pharmacia) using the manufacturer's recommended procedure. The concentrated cell culture fluid was applied first to a control Tris/ethanolamine reacted CNBr-activated Sepharose 4B column and the unbound material applied directly to the fibrinogen-Sepharose column. The contaminating proteins were washed away at room temperature with phosphate buffered saline solution containing 1 mM Ca$^{2+}$, 1 mM Mg$^{2+}$, 25 mM octylglucoside (OG) and 2 mM phenylmethylsulfonylfluoride (PMSF). The bound GPIIb-IIIa was eluted from the column at room temperature with phosphate buffered saline containing 15 mM EDTA, 25 mM OG and 2 mM PMSF. The eluted GPIIb-IIIa was then concentrated by ultrafiltration and the subunits of expected molecular weight identified by autoradiography and by Western blot analysis using monoclonal antibodies specific to GPIIb (3A8) and GPIIIa (4B12). The specificity of the binding to the fibrinogen column is shown by the absence of the protein in the eluate from the control column determined by both methods.

EXAMPLE 4
Expression of LFA-1 and Mac-1 truncations

LFA-1 and Mac-1 are integrins having identical beta chains (beta-2) and distinct alpha chains (alpha L and alpha M, respectively). In this study the full length chains were transformed into host cells. In addition, the DNA encoding the transmembrane domains of the alpha and beta chains of each of these integrins was deleted and the truncated DNAs transformed into host cells for coexpression.

Transformants with full length LFA-1 alphaL chain did not express any detectable cell bound alphaL, but cotranformation with truncated alphaL and truncated beta-2, or with truncated alphaM and truncated beta-2, resulted in the secretion of the truncated heterodimers. Interestingly, transformation with the full length alphaM chain of Mac-1 alone did yield cell surface alphaM. It has not been confirmed that this product represents a stable alphaM monomer since it is conceivable that the recombinant alphaM chain became associated with a beta chain endogenous to the host cell.

We claim:

1. A method for the preparation of a soluble analogue of a naturally occurring multiple subunit polypeptide (MSP),
    wherein the MSP is an integrin comprising an α and a β subunit, said integrin selected from the group consisting of GPIIb-IIIa; p-150,95; Mac-1; LFA-1; a leukocyte adhesion receptor; a member of the VLA family; and a heterodimeric receptor that participates directly in intercellular adhesion or adhesion of cells to extracellular matrix proteins;
    wherein each subunit is encoded by a discrete nucleic acid and wherein at least one subunit comprises a membrane anchor domain, the method comprising:
    1) mutating the nucleic acid encoding one of the subunits which comprises a membrane anchor domain to produce a subunit variant, by modifying or deleting sufficient of the membrane anchor domain to render the membrane anchor domain no longer sufficiently hydrophobic to anchor the subunit variant in a cell membrane;
    2) repeating step 1 for the nucleic acid encoding each subunit comprising a membrane anchor domain;
    3) co-expressing the subunits which do not comprise a membrane anchor domain and the subunit variants of steps 1 and 2 in a host cell;
    4) culturing the host cell of step 3; and
    5) recovering from the host cell culture a biologically active soluble analogue.

2. The method of claim 1 wherein the mutating of step 1 is the substitution of sufficient of the membrane anchor domain with a sufficiently hydrophilic amino acid sequence such that the subunit variant is not anchored in a cell membrane.

3. The method of claim 2 wherein the hydrophilic amino acid sequence comprises an immunoglobulin constant domain.

4. The method of claim 3 wherein a membrane anchor domain is a transmembrane domain.

5. The method of claim 3 wherein the constant domain is a heavy chain constant domain.

6. The method of claim 3 wherein the host cell co-expresses DNA encoding (1) a fusion of a first MSP subunit variant and an immunoglobulin heavy chain constant domain and (2) DNA encoding a second MSP subunit variant which is not fused to an immunoglobulin, the second MSP subunit variant binding directly to the first MSP subunit variant.

7. The method of claim 1 wherein the mutating of step 1 does not comprise the introduction of DNA encoding a multimer forming polypeptide into the DNA encoding the MSP subunits.

8. The method of claim 1 wherein the MSP is GPIIb-IIIa and the recovered soluble GPIIb-IIIa analogue binds fibrinogen, fibronectin, vitronectin or von Willebrand factor.

9. The method of claim 8 wherein the membrane anchor domain is deleted.

10. The method of claim 9 wherein the cytoplasmic domain is deleted.

11. The method of claim 1 wherein the recovered soluble MSP analogue binds to polypeptides containing the sequence RGD.

12. The method of claim 1 wherein the mutating of step 1 comprises inserting, substituting or deleting an amino acid in the membrane anchor domain.

13. The method of claim 12 wherein one of the MSP subunits contains two disulfide bonded polypeptide chains, only one of which comprises a membrane anchor domain.

14. The method of claim 1 wherein the MSP comprises a subunit having the consensus N-terminal sequence Tyr/Phe/Leu-Asn-Leu-Asp, requires a divalent cation for ligand binding, or contains an amino acid domain having substantial sequence homology to the calmodulin calcium binding domain.

15. The method of claim 1, wherein the naturally occurring MSP is a human MSP.

* * * * *